United States Patent [19]

Gradeff et al.

[11] 4,351,962
[45] Sep. 28, 1982

[54] PROCESS FOR THE PREPARATION OF HYDROXY BENZENE CARBOXALDEHYDES

[75] Inventors: Peter S. Gradeff, Pottersville; Stanley T. Murayama, Princeton, both of N.J.

[73] Assignee: Rhone Poulenc Inc., Monmouth Junction, N.J.

[21] Appl. No.: 168,940

[22] Filed: Jul. 11, 1980

[51] Int. Cl.$^3$ .................... C07C 45/36; C07C 45/00
[52] U.S. Cl. .............................. 568/432; 568/433; 568/438; 568/442
[58] Field of Search .............. 568/432, 764, 433, 438

[56] References Cited

U.S. PATENT DOCUMENTS

| | | | |
|---|---|---|---|
| 3,030,428 | 4/1972 | Morris et al. | 568/764 |
| 3,109,033 | 10/1963 | Senior | 568/764 |
| 3,165,496 | 1/1965 | Fusco et al. | 568/764 X |
| 3,673,257 | 6/1972 | Di Bella | 568/432 |
| 4,192,959 | 3/1980 | Bauer et al. | 568/764 |
| 4,199,671 | 10/1978 | Bauer et al. | 568/764 |
| 4,205,188 | 5/1980 | Muench et al. | 568/432 X |
| 4,238,629 | 12/1980 | Bauer et al. | 568/764 |

FOREIGN PATENT DOCUMENTS

987947 3/1965 United Kingdom ............... 568/432

OTHER PUBLICATIONS

Buehler et al, Organic Synthesis, vol. 2, (1977), 59,60,69,70.

*Primary Examiner*—Bernard Helfin

[57] ABSTRACT

A process is provided for the preparation of hydroxy benzene carboxaldehydes having the formula:

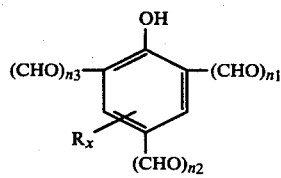

wherein:
R is selected from the group consisting of alkyl, alkoxy, cycloalkyl, aryl, alkoxyalkyl, fluoroalkyl, and hydroxyalkyl oxyalkylene having from one to about twenty carbon atoms; hydroxyalkyl having at least two to about twenty carbon atoms; hydroxy; aldehyde CHO; and halogen;

$n_1$, $n_2$ and $n_3$ are zero or 1; and at least one of $n_1$, $n_2$ and $n_3$ is 1; and x is zero, 1, 2, 3 or 4, which comprises:

(1) condensing with a formaldehyde compound a phenol having the formula:

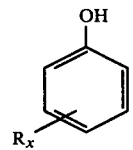

wherein
R is selected from the group consisting of alkyl, alkoxy, hydroxyalkyl, cycloalkyl, aryl, alkoxyalkyl, fluoroalkyl, and hydroxyalkyl oxyalkylene having from one to about twenty carbon atoms; hydroxy; and halogen; and x is zero, 1, 2, 3 or 4, and unsubstituted in at least one ortho or para position in an aqueous reaction medium comprising phenol:HCHO in a molar ratio within the range from about 1:0.1 to about 1:3 and alkali in a molar ratio alkali:phenol within the range from about 1:0.1 to about 1:2 and an alkali concentration not exceeding 30% by weight at a temperature within the range from about 0° to about 120° C. and obtaining a reaction mixture comprising a mixture of monomethylol and polymethylol phenols having the formula:

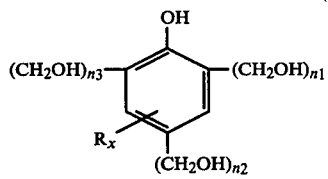

wherein
R is selected from the group consisting of alkyl, alkoxy, hydroxyalkyl, cycloalkyl, aryl, alkoxyalkyl, fluoroalkyl, and hydroxyalkyl oxyalkylene having from one to about twenty carbon atoms; hydroxy; and halogen;

$n_1$, $n_2$ and $n_3$ are zero or 1; and at least one of $n_1$, $n_2$ and $n_3$ is 1; and x is zero, 1, 2, 3 or 4;

(2) subjecting the reaction mixture without separation of the monomethylol species from polymetholol species to oxidation under conditions favoring oxidation of methylol species to the corresponding aldehyde species in the presence of oxygen and an amount of alkali that is at least stoichiometrically equal to the amount of phenol and a platinum or palladium oxidation catalyst, preferably but optionally with a promoter selected from the group consisting of bismuth, lead, silver, tellurium, cadmium, and tin in the form of the metal and/or compounds thereof at a temperature within the range from about 0° to about 100° C. and a pH within the range from about 11 to about 13.5; and then (3) separating and recovering the desired aldehyde in the reaction mixture.

A process also is provided for selectively decarbonylating any undesired aldehyde species to remove all or selected aldehyde groups in certain ring positions, either to yield more desirable aldehyde species or for recycling as starting Material.

28 Claims, No Drawings

PROCESS FOR THE PREPARATION OF HYDROXY BENZENE CARBOXALDEHYDES

Salicylaldehyde, p-hydroxybenzaldehyde, vanillin, and ethyl vanillin are phenolic aldehydes of considerable importance industrially.

Many chemical syntheses are known for their preparation. However, only a few have commercial value and are currently in use.

Vanillin and ethyl vanillin are synthetically prepared by reaction of guaiacol or o-ethoxyphenol with glyoxylic acid, followed by oxidation and decarboxylation:

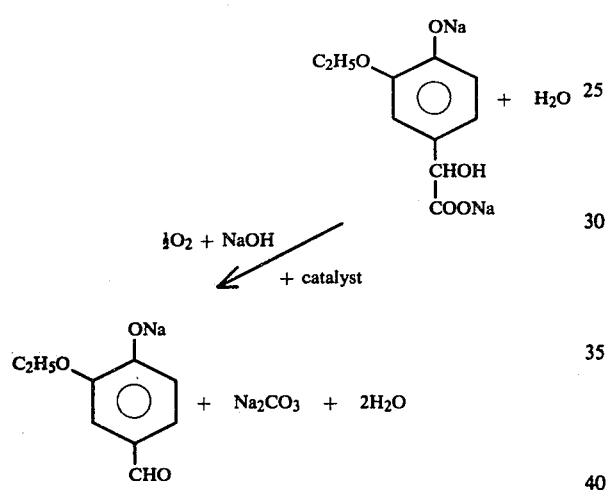

Glyoxylic acid is expensive, and the overall process is quite complicated. Nevertheless, this is the preferred process today, and the literature indicates that considerable work has been done to apply the process for the preparation of other phenolic aldehydes as well.

Most of the salicylaldehyde produced in the world today is made by first reacting phenol with boric acid, followed by condensation with formaldehyde and saponification, then followed by oxidation of the sodium saligenate to the aldehyde, which is liberated upon neutralization.

Marchand and Grenet U.S. Pat. Nos. 3,290,352 and 3,290,393, patented Dec. 6, 1966, note that British Pat. No. 774,696 condenses phenol, meta-cresol or meta-ethylphenol with formaldehyde in aqueous medium in the presence of zinc acetate or cadmium formate. Starting with phenol, the best yield of pure saligenol obtained is 21%.

H. G. Peer, Rec. Trav. Chim. 79 825 (1960) discloses that saligenol is obtained by reacting paraformaldehyde with phenol in benzene in the presence of boric acid. An orthoboric ester is intermediately formed, to which the formaldehyde becomes fixed with the formation of a complex which may be hydrolyzed to give phenol and saligenol. The reaction may be represented as follows:

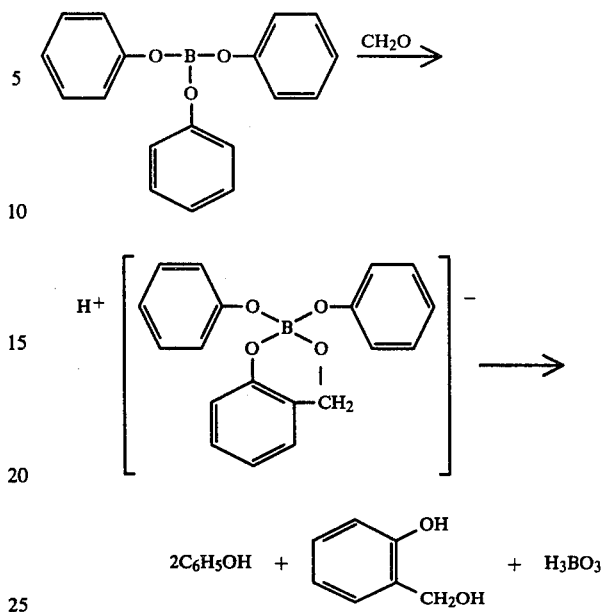

Instead of boric acid, triphenylorthoborate may also be used as a catalyst. However, the quantities of saligenol formed are small, and the isolation of pure saligenol from the mixture is difficult. Only 1 g of pure saligenol was obtained from 20 g of phenol, 4.66 g of paraformaldehyde and 10 g of boric acid, i.e., a yield of about 5%.

Marchand and Grenet claim to obtain in very good yields saligenol and its nuclearly substituted derivatives by reacting a triphenyl metaborate, in which each phenyl group has at least one unsubstituted position ortho to the borate ester link, with formaldehyde, or a substance which generates formaldehyde under the conditions of the reaction, and decomposing the tri(ortho-hydroxybenzyl)metaborate produced to liberate the ortho-hydroxybenzyl alcohol. Ordinarily, the triphenyl metaborate is unsubstituted or substituted on each phenyl group by up to three substituents which are alkyl or alkoxy groups or halogen atoms. The alkyl and alkoxy groups which may be attached to the phenyl group may be any alkyl or alkoxy group having from one to twelve, preferably one to six, carbon atoms, more especially a methyl, ethyl, propyl, butyl, pentyl or hexyl group. The halogen substituents may be chloro, bromo or iodo radicals.

The ortho-hydroxybenzyl alcohol that is obtained can be oxidized by any available procedure to form the corresponding aldehyde. Marchand and Grenet, U.S. Pat. No. 3,321,526, patented May 23, 1967, disclose the preparation of salicylaldehyde by oxidizing the salicyl alcohol with oxygen using a palladium catalyst.

Marchand and Grenet note several processes for the preparation of certain o-hydroxybenzaldehydes, especially salicylic aldehyde, from the corresponding o-hydroxybenzyl alcohol:

(i) Oxidation of o-hydroxybenzyl alcohol with platinum black in the presence of air [Piria Liebigs Ann. 56 42 (1845)];

(ii) Oxidation of the alcohol in aqueous solution with potassium chromate in the presence of sulphuric acid (ibidem); and (iii) Oxidation of the alcohol in chloroform solution with active manganese dioxide (Dutch Patent No. 87,141).

The first two methods, for which no yield is given, are given in the scientific literature (Beilstein, Vol. 8 p. 31) as methods of formation without any industrial interest.

The third method gives a relatively low yield and involves the use of considerable quantities of a reactant which, in order to be sufficiently active, must be prepared from costly products such as potassium permanganate.

Marchand et al note that it is also known to oxidize primary aromatic alcohols with air in the presence of either platinum deposited on charcoal, or platinum dioxide [Heyns and Blazezewicz, Tetrahedron 9 67 to 75 (1960)]. These authors show that the oxidation of primary aromatic alcohols with oxygen in the presence of a platinum catalyst gives an aldehyde when the operation is carried out in a purely organic medium while in an aqueous medium the oxidation proceeds as far as the corresponding carboxylic acid. Thus, in the case of benzyl alcohol, oxidation in an n-heptane medium gives benzaldehyde, while in an aqueous medium and in the presence of a little sodium hydroxide, benzoic acid is obtained almost quantitatively.

Marchand et al oxidize hydroxybenzyl alcohols of the formula:

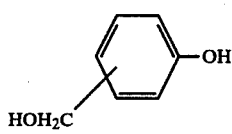

in which the —CH$_2$OH radical is in the ortho, meta or para position and the benzene nucleus may be substituted by halogen, alkyl, or alkoxy radicals, to the corresponding benzaldehydes, with a palladium catalyst, which not only results in a rapid and almost complete absorption of oxygen, but also limits the oxidation to the aldehyde stage without any appreciable formation of the acid.

The alkyl and alkoxy groups in the compounds of Formula I may contain from one to twelve carbon atoms, and include, more especially, the methyl, ethyl, propyl, butyl, pentyl and hexyl groups. The halogen atoms may be more especially chlorine, bromine or iodine atoms.

The oxidation is carried out by passing oxygen or a gas containing oxygen, e.g., air, through an aqueous, preferably alkaline, solution of the hydroxybenzyl alcohol containing the catalyst in suspension at atmospheric pressure or at superatmospheric pressure.

In a variation of the Marchand et al process, Gay and Raymond, U.S. Pat. No. 3,780,110, patented Dec. 18, 1973, provided an integrated method for preparing 3-fluorosalicylaldehyde by reacting ortho-fluorophenol with a boron-containing compound and a formaldehyde source material.

This process reacts an ortho-fluorophenol with a selected boron-containing compound and a selected formaldehyde source material to produce 3-fluorosalicylaldehyde as shown by the following equation wherein boron oxide and trioxane are used as reactants:

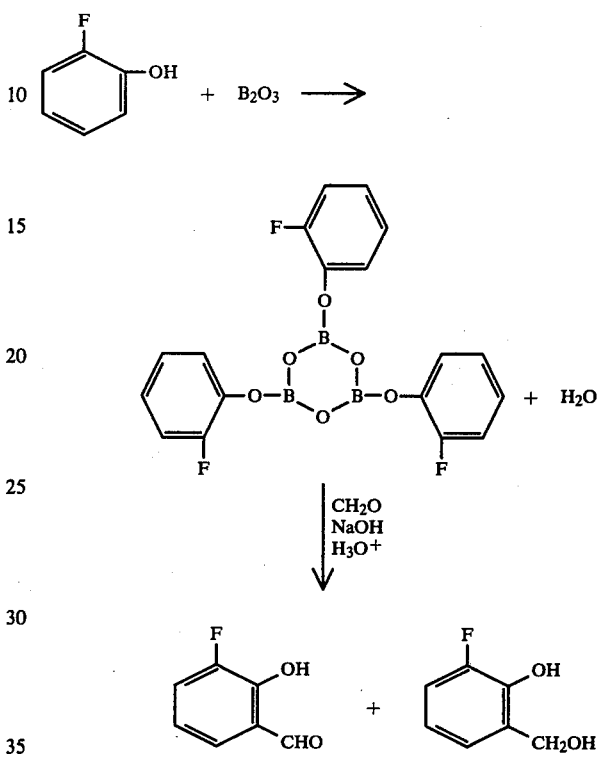

The 3-fluorosalicyl alcohol which is produced by the above-noted reaction can be readily oxidized to 3-fluorosalicylaldehyde by known oxidation techniques and also by the method as disclosed in the copending application by Walter A. Gay and Maurice A. Raymond entitled "Method for Preparing Aromatic Aldehydes", application Ser. No. 224,272.

The concentration level of unreacted formaldehyde must be kept fairly low in order to avoid undesired resin formation. The temperature of the reaction with formaldehyde must be maintained above a particular level in order to increase the rate of selective ortho reaction and to decrease resin formation. More particularly, this temperature should be maintained at a minimum of about 90° C. Additionally, the pH of the final reaction mixture after the hydrolysis-acidification steps must be controlled to minimize resin formation.

Another well known process still in use is the Reimer-Tiemann process. The Reimer-Tiemann process produces both salicylaldehyde and p-hydroxybenzaldehyde together. Phenol is reacted with chloroform in the presence of an alkali metal base under controlled conditions, substituting a CHCl$_2$ group on the phenol in the form of the sodium phenolate in either the ortho or the para position to the ONa group, resulting in the concommitant production of both salicylaldehyde and p-hydroxybenzaldehyde according to the following reaction:

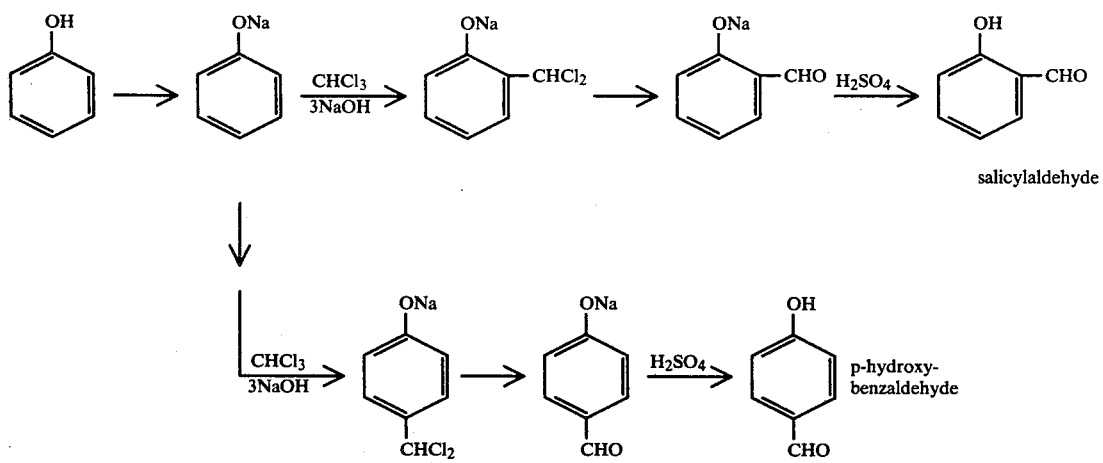

salicylaldehyde p-hydroxy-
benzaldehyde

This reaction is not, however, completely satisfactory. Pontz U.S. Pat. No. 3,365,500, patented Jan. 23, 1968, points out that although the reaction has been intensively investigated over the years, it has never been found possible to increase the yield of salicylaldehyde and p-hydroxybenzaldehyde above about 50 to 60% of the theoretical. The hydroxybenzaldehyde mixture that is obtained is composed of about five parts of salicylaldehyde to one part of p-hydroxybenzaldehyde, which means that if one really wants p-hydroxybenzaldehyde, one has to dispose of a considerable excess of salicylaldehyde. Moreover, the remainder of the reaction product is tar, and is entirely lost.

Pontz indicates that various solvents or mixtures of solvents have been proposed to serve as reaction media. Aqueous ethyl alcohol for instance was proposed for insoluble phenols such as nitrophenol and naphthol. Traub German Pat. No. 80,195 uses 95% ethyl alcohol as the reaction solvent for the production of hydroxyaldehydes, particularly vanillin, and claims improved yields, lessened tar formation, and increased production of the p-hydroxybenzaldehyde isomer. However, Friedlander's Fortschritte der Teerfarbenfabrikation vol 4, page 1289 (1894-7) comments that the yield of hydroxyaldehydes from the Traub process is very unsatisfactory, and scarcely better than that using the original Reimer-Tiemann conditions.

Sen et al J. Indian Chem. Soc. 9 173 (1932) state that the use of chloroform in an ethyl alcohol solution in the Reimer-Tiemann reaction increases the yield of aldehyde. However, the only example describing the reaction of phenol with chloroform and sodium hydroxide in aqueous ethyl alcohol shows a combined yield for salicylaldehyde and p-hydroxybenzaldehyde of only 33%, based on the phenol reacted. The proportion of salicylaldehyde to p-hydroxybenzaldehyde in the product is about five to one, the same as for the conventional aqueous reaction.

Pontz suggests that the use of aqueous methanol as the solvent medium produces better combined yields of the hydroxyaldehydes, and sharply reduced tar formation. The Examples show an approximately 2 to 1 ratio of salicylaldehyde to p-hydroxybenzaldehyde; and 83.9% yield of the combined aldehydes, with a 57.4% yield of salicylaldehyde and 26.5% yield of p-hydroxybenzaldehyde, is claimed in Example 1. The other Examples show considerably less p-hydroxybenzaldehyde, however, and thus this process is not entirely satisfactory, either, for the production of p-hydroxybenzaldehyde.

DiBella, U.S. Pat. No. 3,673,257, patented June 27, 1972, points out that o-hydroxybenzyl alcohol (saligenin) can be oxidized in the presence of a platinum catalyst to produce salicylaldehyde. However, DiBella states that the reported processes are generally unsatisfactory for use on a commercial scale, because they require the use of large amounts of the catalyst if the necessary reaction rate is to be attained, give low yields of salicylaldehyde, and under certain conditions salicylic acid rather than salicylaldehyde is formed. In U.S. Pat.No. 2,676,189 Britton and Head state that when saligenin was oxidized under a variety of conditions using a platinum or platinum oxide catalyst, it was not possible to convert more than fifteen percent of the saligenin to salicylaldehyde. Marchand and Genet report in U.S. Pat. No. 3,321,526 that when saligenin was oxidized in the presence of boric acid and a platinum catalyst a 12.5% yield or salicylaldehyde was obtained, whereas when a palladium catalyst was used under the same conditions the yield of salicylaldehyde was 83.5%.

DiBella accordingly proposes that hydroxybenzyl alcohols be converted to hydroxybenzaldehydes by contacting the alcohols with an oxygen-containing gas in the presence of a platinum catalyst and certain cationic oxidation promoters. The use of the cationic oxidation promoters results in a substantial increase in the rate at which the hydroxybenzyl alcohol is oxidized and thus permits a corresponding reduction in the amount of the platinum catalyst that must be used to achieve a commercially-feasible rate of reaction.

U.S. Pat. No. 4,119,671, patented Oct. 10, 1978 to Bauer, Molleken, Flege and Wedemeyer, and Belgian Pat. No. 854,334 to Bayer A. G. provide a process for the oxidation of hydroxybenzyl alcohols with oxygen or oxygen-containing gases in the presence of a platinum metal catalyst, with the addition of lead, silver, tellurium and/or tin, and/or compounds thereof, as an activator. The activator permits a considerable reduction in the consumption of the platinum metal, inhibits the formation of resin during the oxidation, and also permits reduction of the amount of alkali required, in addition to giving a shorter reaction time and a higher yield of the aldehyde. The hydroxybenzyl alcohols have the general formula:

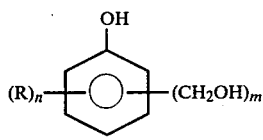

in which m represents 1, 2 or 3, n represents the number which results from the difference (5—m) and the radicals R independently of one another represent hydrogen, alkyl, aryl, alkoxy, hydroxyl, halogen, carboxyl or a fused ring.

These hydroxybenzyl alcohols are known, or can be prepared by known processes, as exemplified by the reaction of phenol with one or several moles of formaldehyde, described by Walker, Formaldehyde Third Edition (1964) pp 304 et seq, and German Auslegeschrift No. 1,261,517. Mixtures of different hydroxybenzyl alcohols can be employed for the oxidation, and it is possible to selectively oxidize one or two of the various hydroxymethyl groups present, when there is more than one. The products are hydroxybenzaldehydes, which contain unchanged hydroxymethyl groups.

German Offenlegungsschrift No. 2,620,254 to Bayer A. G. describes a rather similar process, but in addition to lead, silver, tellurium and tin, bismuth and bismuth compounds are suggested as activators.

Le Ludec, U.S. Pat. No. 4,026,950, patented May 31, 1977, describes a process for the production of hydroxybenzaldehydes and especially salicylaldehydes from the oxidation of the corresponding hydroxybenzyl alcohol, especially o-hydroxybenzyl alcohol. The hydroxybenzyl alcohol is oxidized in the liquid phase with molecular oxygen or a gas-containing molecular oxygen in an aqueous medium containing an alkaline agent in the presence of a platinum or palladium catalyst and in the presence of a co-catalyst containing bismuth.

Phenol also reacts with formaldehyde, to produce methylol phenols en route to the more complex phenol-formaldehyde resins. Kirk-Othmer *Encyclopedia of Chemical Technology*, Third Edition, Volume 15, p. 176 (1968), shows the current understanding of the enormous complexity of the reactions between phenol and a formaldehyde.

The condensation of phenols with formaldehyde can be carried out either in aqueous or nonaqueous medium, using a solution of either formaldehyde or paraformaldehyde. A variety of catalysts have been proposed, ranging from strong alkalies to salts of metals with organic acids. Considerable data can be found in the literature on the mechanism and kinetics of the reaction and the composition of the reaction mixture, and showing the difficulties in analyzing the reaction mixture, the difficulties in isolating the methylol phenols from the reaction mixture, and above all the high tendency of the reaction products to condense further to form phenol-formaldehyde polymers upon heating or chemical treatment.

The fact is that this reaction proceeds so readily, and is so difficult to control and arrest at the methylol phenol stage, that one invariably obtains a host of reaction byproducts, and as a result this reaction has never been utilized commercially as a practical synthesis for the quantity production of hydroxybenzyl alcohols.

Sprengling and Freeman, *Journal of the American Chemical Society* 72 1982-85 (1950), noted that it is generally agreed that the first isolatable products of the alkali-catalyzed reaction between phenols and formaldehyde in aqueous solution are the hydroxybenzyl alcohols, or methylol phenols, and that it seems very probable that this is the initial reaction in the formation of phenol-formaldehyde resins. However, prior to Sprengling and Freeman's work, study of the reaction of phenols with formaldehyde leading to methylol phenols had been restricted almost entirely to substituted phenols, because they are slower in both the initial and subsequent reactions, and because only a small number of methylol derivatives is possible, due to the substituents blocking addition of methylol groups in their positions of the phenol ring.

Theoretically, phenol can react with formaldehyde in only the ortho and para-positions, with a possible yield of two isomeric monomethylols, the ortho and para derivatives, two isomeric dimethylols, and one trimethylol derivative. So far as is known, there is no reaction in the meta position. However, prior to Sprengling and Freeman's work, of these five methylol phenols, only the ortho isomer, saligenin, and the para isomer, p-hydroxybenzyl alcohol or p-methylol phenol, had ever been isolated, although fractions supposed to contain the polymethylol derivatives had been obtained.

The preparation and isolation of the ortho and para methylol derivatives of phenol was first accomplished in 1894 by two independent investigators, Manasse Ber 27 2409 (1894) and Lederer, J. prakt Chem. 50 223 (1894). Both Manasse and Lederer used alkali as the catalyst. Lederer used heat in the presence of a small amount of base, whereas Manasse employed an approximately equimolar amount of strong alkali and phenol, and allowed the reaction to take place at ordinary room temperature.

In the Manasse procedure, phenol is dissolved in somewhat more than an equivalent amount of dilute sodium hydroxide, and a molecular quantity of commercial 37% aqueous formaldehyde is added. The reaction mixture is then allowed to stand at room temperature for one day or more, until the odor of formaldehyde had disappeared. Then the solution is neutralized with acetic acid and extracted with ether, which removes the methylol phenols and unreacted phenol. The latter is removed by steam distillation, leaving the mixture, consisting principally of saligenin, the ortho isomer, and p-methylol phenol, the para isomer. Saligenin may be isolated from this anhydrous mixture by extraction with benzene at 50° C.

According to Granger, *Ind. Eng. Chem.* 24 442-8 (1932), only two-thirds of the phenol is alkali-catalyzed reactions of equimolar quantities of phenol and formaldehyde in aqueous solutions reacts, although all of the formaldehyde is consumed. This shows that substantial amounts of polymethylol phenols are formed as byproducts, and remain in the reaction mixture, from which they are not extracted, since they are more soluble in water than in ether. Granger isolated three liquid phenol alcohol fractions believed to represent the three isomeric methylol phenols, and postulated three possible polyalcohols, as follows:

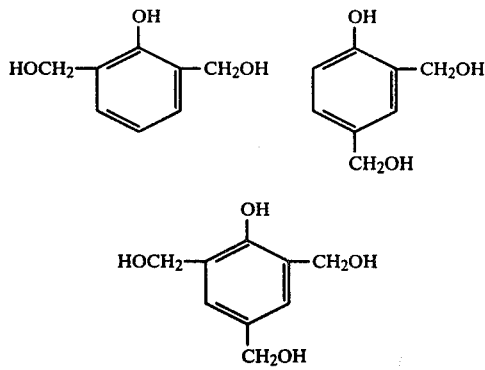

Granger points out that in order to be successful in obtaining the monomethylol derivatives, and limit the reaction to the phenol alcohol stage, both Manasse and Lederer had to control the reaction, using low temperature, in the case of Manasse, and shortening reaction time, in the case of Lederer. Ultimately, the Manasse method was adopted as the standard method for the preparation.

Sprengling and Freeman studied the relative proportions of methylol phenols in the reaction product under the particular phenol to formaldehyde ratio which they used, 1:1.4. This ratio Staeger and Biert Helv Chim Acta 21 641 (1938) found best suited for the the isolation of p-hydroxybenzyl alcohol (and this ratio also falls within the range of most commercial applications of the process). Sprengling and Freeman catalyzed the reaction with sodium hydroxide in an amount a little more than that equivalent to the phenol used, and ran the reaction at room temperature. This, Sprengling and Freeman state, gave the highest possible yields of methylol phenols, and resulted in the reaction mixture having the proportions set out in Table II:

TABLE II

| Components of Reaction Product | Mole % present |
|---|---|
| Phenol | 5–10 |
| o-Methylolphenol | 10–15 |
| p-Methylolphenol | 35–40 |
| 2,4-Dimethylolphenol | 30–35 |
| 2,6-Dimethylolphenol | None |
| 2,4,6-Trimethylolphenol | 4–8 |

Freeman & Lewis, J. Am. Chem. Soc. 76 2080–2087 (1954) confirmed that this is so, and state at page 2085:

"As a result of the varying degrees of reactivity here observed, we may predict that in a reaction between phenol and less than three equivalents of formaldehyde, saligenin will be the first product formed in appreciable quantity. However, its forward reaction will be about as rapid as its rate of formation, as soon as its concentration approaches that of the remaining phenol. Thus, its concentration will not appear to increase but will appear to remain static in the mixture. And finally, it will be the first of the methylolphenols to disappear.

"The p-monomethylolphenol will appear in detectable quantity somewhat later than the ortho isomer but, due to its low reactivity, its concentration will increase steadily until the supply of phenol is exhausted. 2,4-Dimethylolphenol will appear still later. However, because of its relatively reduced tendency toward subsequent reaction, and its formation from two sources, it will rapidly become a major component of the mixture. 2,6-Dimethylolphenol will react further almost as rapidly as it is formed. Hence, it will seldom be found in detectable amounts in normal resin mixtures. Concentration of 2,4,6-trimethylolphenol will increase rapidly, but only to the extent that the available concentration of formaldehyde will permit.

"Thus, in general, p-hydroxybenzyl alcohol and 2,4-dimethylolphenol will be the major components of any formaldehyde-deficient mixture (below 3:1, formaldehyde:phenol). Saligenin will be a minor component, 2,6-dimethylolphenol concentration will be below the limits of detection, and the relative amounts of trimethylol phenol and residual phenol will be determined by the amount of formaldehyde available."

It is apparent that this reaction mixture is so complex that the combination of this reaction with the oxidation of the methylolphenol does not on its face provide an acceptable alternative to the Reimer-Tiemann process or to the phenol boric acid oxidation process for the preparation of p-hydroxybenzylaldehyde.

EPO patent application No. 0,000,165 to Haarman and Reimer GmbH, published Jan. 10, 1979, describes a process for the preparation of pure o-hydroxybenzyl alcohol and p-hydroxybenzyl alcohol, either separately or in admixture, by reaction of phenol and formaldehyde in the presence of basic catalysts, isolating the hydroxybenzyl alcohols in an at least two-step countercurrent solvent extraction with water and/or a water-immiscible organic solvent. The patentees note that in British Pat. No. 751,845, saligenin, o-hydroxybenzyl alcohol, is extracted from the reaction mixture of phenol with formaldehyde in the presence of basic catalysts using benzene, and a 50% yield is claimed. British patent No. 774,696 separates the o-hydroxybenzyl alcohols from this reaction mixture by fractional crystallization, and claims a 21% yield. U.S. Pat. No. 2,804,480 describes a more complicated procedure, using trimethyl chlorosilane.

Davis and Weck U.S. Pat. No. 3,981,929, patented Sept. 21, 1976, describe a method of separating methylolphenols from an organic solution containing the methylolphenols by contacting the organic solution with an aqueous alkaline borate solution in which lithium ions are present in a quantity greater than any other single alkali metal ion for a period of time sufficient to form a solid complex of the lithium and boron with the methylolphenols which then are separated from the organic solution.

The methylolphenols subsequently may be recovered from the complex by decomposing the complex with acid and dissolving the released methylolphenols in an organic solvent.

All of these extraction procedures are however complicated and expensive to carry out, and only yield a methylolphenol that still has to be oxidized in another step to the corresponding aldehyde. Thus, this combination of reaction steps does not result in a process that is competitive with those already in use, such as the Reimer-Tiemann process or the phenol boric acid oxidation process, which despite their problems remain the standards that must be met, if a competitive process is to be successful.

Now in accordance with the invention it has been determined that it is possible to subject the reaction mixture obtained by the condensation of a formaldehyde compound with a phenol in an aqueous alkaline reaction medium to a catalytic oxidation without separation of the monomethylol species from the polymethylol species or other reaction products, or optionally, starting phenol, if the condensation reaction and the catalytic oxidation reaction are carried out under certain limited conditions that themselves are an important feature of the invention. Oxidation both of monomethylol species to monoaldehyde species and of polymethylol species to polyaldehyde species is readily obtained. Due to the fact that it is not necessary to separate the monomethylol species from the polymethylol species prior to oxidation, it becomes feasible to utilize the phenol-formaldehyde condensation reactions in the presence of an alkaline catalyst for the preparation of hydroxyaldehydes.

The reaction mixture obtained by oxidation of such a starting material of course contains a number of mono and poly aldehyde species corresponding to the methylol species present. Another important aspect of the present invention is the development of a technique for the separation of the various species from this reaction mixture that permits recovery of the desired monoaldehyde products without a reduction in yield.

As a further feature of the invention, a process is provided for the selective decarbonylation of any unwanted monoaldehyde and polyaldehyde species present in the reaction mixture, after separation of the desired aldehyde species, selectively to remove all aldehyde groups or only selected aldehyde groups in certain ring positions, to convert them to desired aldehyde species, or to the starting phenol for recycling as starting phenol to the condensation reaction, thus reducing reagent losses in side reactions and materially increasing the efficiency as well as lowering the cost of the synthesis.

Also important, of course, is control of the condensation reaction of phenol with formaldehyde so as to obtain a reaction mixture containing predominantly the desired methylol phenols in preference to other species, with a minimum of higher polymeric reaction products, such as phenol-formaldehyde polymers of varying molecular weight.

The process of the invention is applicable not only to phenol but also to ring-substituted phenols as a class having at least one ortho or para position available for substitution of a methylol group and then conversion of the methylol group to an aldehyde group. Any substituent on the phenol ring should however be inert, so that it does not interfere with the methylol substitution and oxidation to aldehyde groups in the synthesis.

Thus, in accordance with the invention, a process is provided for the preparation of hydroxy benzene carboxaldehydes having the formula:

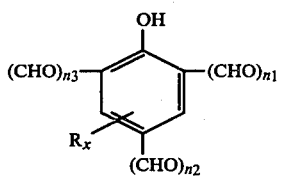

wherein:
R is selected from the group consisting of alkyl, alkoxy, cycloalkyl, aryl, alkoxyalkyl, fluoroalkyl, and hydroxyalkyl oxyalkylene having from one to about twenty carbon atoms; hydroxyalkyl having at least two to about twenty carbon atoms; hydroxy; aldehyde CHO; and halogen;

$n_1$, $n_2$ and $n_3$ are zero or 1; and at least one of $n_1$, $n_2$ and $n_3$ is 1; and x is zero, 1, 2, 3 or 4, which comprises:

(1) condensing with a formaldehyde compound a phenol having the formula:

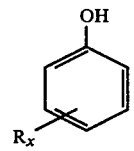

wherein
R is selected from the group consisting of alkyl, alkoxy, hydroxyalkyl, cycloalkyl, aryl, alkoxyalkyl, fluoroalkyl, and hydroxyalkyl oxyalkylene having from one to about twenty carbon atoms; hydroxy; and halogen; and x is zero, 1, 2, 3 or 4, and unsubstituted in at least one ortho or para position in an aqueous reaction medium comprising phenol:HCHO in a molar ratio within the range from about 1:0.1 to about 1:3 and alkali in a molar ratio alkali:phenol within the range from about 1:0.1 to about 1:2 and an alkali concentration not exceeding 30% by weight at a temperature within the range from about 0° to about 120° C. and obtaining a reaction mixture comprising a mixture of monomethylol and polymethylol phenols having the formula:

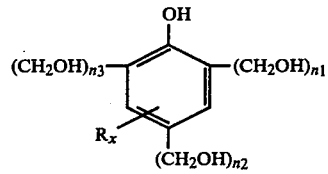

wherein
R is selected from the group consisting of alkyl, alkoxy, hydroxyalkyl, cycloalkyl, aryl, alkoxyalkyl, fluoroalkyl, and hydroxyalkyl oxyalkylene having from one to about twenty carbon atoms; hydroxy; and halogen;

$n_1$, $n_2$ and $n_3$ are zero or 1; and at least one of $n_1$, $n_2$ and $n_3$ is 1; and x is zero, 1, 2, 3 or 4;

(2) subjecting the reaction mixture without separation of the monomethylol species from polymethylol species to oxidation under conditions favoring oxidation of methylol species to the corresponding aldehyde species in the presence of oxygen and an amount of alkali that is at least stoichiometrically equal to the amount of phenol and a platinum or palladium oxidation catalyst, preferably but optionally with a promoter selected from the group consisting of bismuth, lead, silver, tellurium, cadmium, and tin in the form of the metal and/or compounds thereof at a temperature within the range from about 0° to about 100° C. and a pH within the range from about 11 to about 13.5; and then (3) separating and recovering the desired aldehyde in the reaction mixture.

A process also is provided for selectively decarbonylating any undesired aldehyde species to remove all or selected aldehyde groups in certain ring positions, either to yield more desirable aldehyde species or for recycling as starting material.

Exemplary R alkyl groups falling within the above formula include ethyl, methyl, propyl, isopropyl, butyl, isobutyl, secondary butyl, tertiary butyl, amyl, isoamyl, tertiary amyl, hexyl, isohexyl, tertiary hexyl, secondary hexyl, heptyl, isoheptyl, octyl, 2-ethyl hexyl, isooctyl, nonyl, isononyl, decyl, undecyl, dodecyl, tetradecyl, hexadecyl, octadecyl, and eicosyl.

Exemplary R alkoxy include oxyethyl, oxymethyl, oxypropyl, oxyisopropyl, oxybutyl, oxyisobutyl, oxy-sec-butyl, oxy-t-butyl, oxyamyl, oxyisoamyl, oxy-t-amyl, oxyhexyl, oxyisohexyl, oxy-t-hexyl, oxy-sec-hexyl, oxyheptyl, oxyisoheptyl, oxyoctyl, oxy-2-ethyl hexyl, oxyisooctyl, oxynonyl, oxyisononyl, oxydecyl, oxyundecyl, oxydodecyl, oxyhexadecyl, oxytetradecyl, and oxyoctadecyl.

Exemplary R hydroxyalkyl include hydroxyethyl, hydroxymethyl, hydroxypropyl, hydroxyisopropyl, hydroxybutyl, hydroxyisobutyl, hydroxy-sec-butyl, hydroxy-t-butyl, hydroxyamyl, hydroxyisoamyl, hydroxy-t-amyl, hydroxyhexyl, hydroxyisohexyl, hydroxy-t-hexyl, hydroxy-sec-hexyl, hydroxyheptyl, hydroxyisoheptyl, hydroxyoctyl, hydroxy-2-ethyl hexyl, hydroxyisooctyl, hydroxynonyl, hydroxyisononyl, hydroxydecyl, hydroxyundecyl, hydroxydodecyl, hydroxyhexadecyl, hydroxyoctadecyl, and hydroxyeicosyl.

Exemplary R cycloalkyl include cyclobutyl, cyclopentyl, cyclohexyl, cycloheptyl, cyclooctyl and cyclododecyl.

Exemplary R fluoroalkyl include fluoromethyl, difluoromethyl, trifluoromethyl, fluoroethyl, 1,1,1-trifluoroethyl, pentafluoroethyl, fluoropropyl, fluorobutyl, trifluoroamyl, fluorooctyl, fluorodecyl, and fluorooctadecyl.

Exemplary R hydroxyalkyl oxyalkylene include hydroxymethyl oxyethylene, hydroxyethyl di-(oxyethylene), hydroxyethyl tri-(oxyethylene), hydroxyethyl oxypropylene-1,2; hydroxyethyl oxybutylene, hydroxypropyl oxypropylene, hydroxybutyl oxybutylene, hydroxybutyl di-(oxybutylene) and hydroxypentyloxypentylene.

Exemplary halogen include fluorine, chlorine, bromine and iodine.

Phenols which undergo the reaction include phenol, o, m, and p-cresol; o, m and p-ethyl phenol; o, m and p-isopropyl phenol; o, m and p-butyl-phenol; o, m and p-n-octyl phenol; o, m and p-2-ethylhexyl phenol; o, m and p-decylphenol; o, m and p-octadecylphenol and o, m and p-eicosyl phenol; o, m and p-ethoxy phenol; o, m and p-propoxy phenol; o, m and p-butoxyphenol; o, m and p-hexoxyphenol; o, m and p-decoxyphenol; o, m and p-hexadecoxyphenol and o, m and p-octadecoxyphenol; o, m and p-hydroxyethyl phenol; o, m and p-hydroxypropyl phenol; o, m and p-hydroxyhexyl phenol; o, m and p-hydroxydecyl phenol; o, m and p-cyclopropyl phenol; o, m and p-cyclobutyl phenol; o, m and p-cyclopentyl phenol; o, m and p-cyclohexyl phenol; o, m and p-cycloheptyl phenol; o, m and p-cyclooctyl phenol; o, m and p-phenyl phenol; o, m and p-methoxymethyl phenol; o, m and p-ethoxyethyl phenol; o, m and p-propoxypropyl phenol; o, m and p-butoxymethyl phenol; o, m and p-hexoxyethyl phenol; o, m and p-hydroxyethyloxyethylene phenol; o, m and p-hydroxyethyl dioxyethylene phenol; resorcinol, hydroquinone, pyrogallol, orcinol, cresol, catechol, carvacrol, o-xylenol, m-xylenol, sym-xylenol, and p-xylenol.

All of the above phenols produce aldehydes in which at least one of the open ortho and para positions become substituted with an aldehyde group.

The process in accordance with the invention is thus a synthesis of hydroxy benzene carboxaldehydes from the corresponding unsubstituted or substituted phenols, and includes two reaction steps which can be outlined as follows:

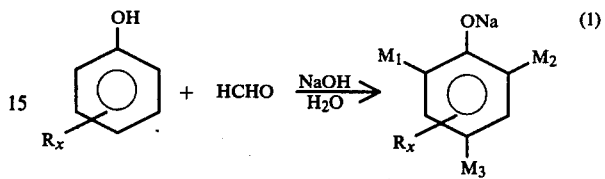

(1)

M = CH$_2$OH

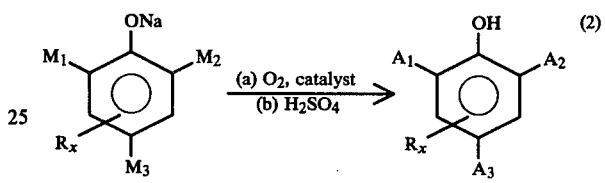

(2)

A = CHO

In addition to these reactions, there can also be applied the selective decarbonylation reaction of the undesired aldehydes obtained as a byproduct in Step (2) of the synthesis, which results in regeneration of the starting phenol, or selected aldehyde species. The decarbonylation reactions are represented below:

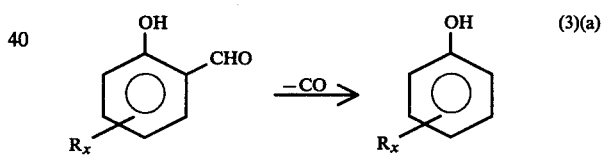

(3)(a)

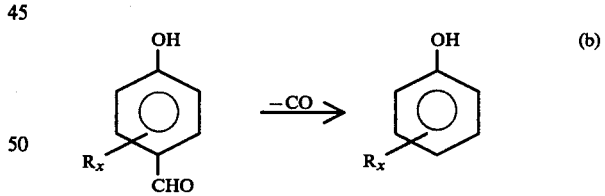

(b)

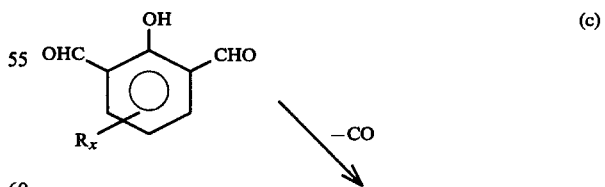

(c)

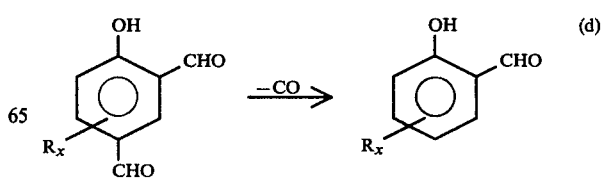

(d)

-continued

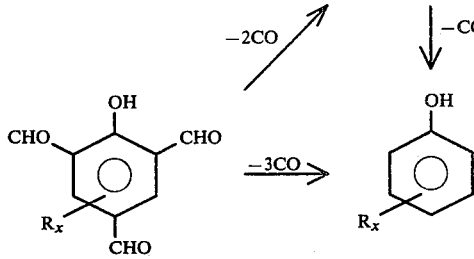

(e)

While the process of the invention is of primary application to the preparation of salicylaldehyde and p-hydroxybenzaldehyde, it can also be employed in the preparation of selected substituted hydroxybenzaldehydes containing one or more substituents of the type of R above. o-Methoxy phenol gives vanillin in the synthesis of the invention, and o-ethoxyphenol gives ethyl vanillin.

The condensation reaction between phenol and formaldehyde proceeds in the presence of water and alkali. Consequently, it is usually convenient to employ an aqueous solution of formaldehyde in a formaldehyde concentration within the range from about 20 to about 37%. While formaldehyde is normally used, compounds that give rise to formaldehyde, such as paraformaldehyde can be substituted, in equivalent amount.

The molar ratio of phenol to formaldehyde influences the course of the reaction and should be within the range phenol:HCHO from about 1:0.1 to about 1:3, and preferably within the range from about 1:0.2 to about 1:3. At ratios of phenol:formaldehyde providing more formaldehyde than the stoichiometric 1 to 1 ratio, the proportion of polymethylol phenols may increase, but if these are decarbonylated to phenol and then recycled, this is of minor importance. The higher the ratio of phenol to formaldehyde, the higher the yield of monomethylol compounds, based on the amount of phenol converted, and thus such ratios are advantageous, even when the polymethylol derivatives are an undesired byproduct.

The condensation reaction requires an alkali catalyst to convert at least a proportion of the phenol to the corresponding methylol phenols. The molar ratio of alkali:phenol should be within the range from about 1:0.1 to about 1:2, and preferably within the range from about 1:0.8 to about 1:1.2. The amount and nature of the alkali influences the ratios of o- and p-methylol isomers in the reaction product, as well as the speed of the reaction. The alkali is used in the form of an aqueous solution at an alkali concentration ranging up to about 30%.

As the alkali, any alkali metal or alkaline earth metal hydroxide can be used, such as sodium hydroxide, lithium hydroxide, potassium hydroxide, barium hydroxide, and calcium hydroxide.

While the mode of addition of the reactants and the order of addition are not critical, it is usually preferred to add the aqueous alkali solution to the phenol, and then to add the aqueous formaldehyde solution. Heat can then be applied, if desired, and reaction continued until the methylol phenol derivatives are formed.

The reaction proceeds at low temperatures, ranging from about 0° C. up to about 100° C., but is preferably carried out within the range from about 50° to about 75° C. The reaction is usually complete, that is, all of the formaldehyde has been consumed, when not in excess, after a reaction time within the range from about one-half hour to about fifteen hours.

Oxidation of the methylol phenols to the corresponding phenolic aldehydes is carried out directly on the reaction mixture from the condensation step without isolation or separation of the reaction products. However, the amount of alkali is at least stoichiometric to the phenol, and preferably is adjusted to an at least 10% excess. Larger amounts of alkali are to be used if unreacted formaldehyde is present in the reaction mixture. Thus, if the amount of alkali is below this, it is necessary to add alkali to the reaction mixture. The upper limit on the phenol:alkali ratio is about 1:2, and preferably the ratio is within the range from about 1:1.1 to about 1:2.

The amount of alkali should be sufficient to bring the pH of the reaction mixture to within the range from about 11 to about 13.5. If desired, any alkali in excess of the stoichiometric amount can be added during the course of the oxidation reaction.

The amount of water is not critical, and is usually within the range from about 3 to about 30 moles per mole of phenol. More can be used, however, if desired. A range that is preferred in many instances is from about 6 to about 10 moles per mole.

Following the adjustment of alkali concentration, the oxidation catalyst and promotor are added. The catalyst is platinum or palladium supported on an inert carrier and the promoter is selected from the group consisting of bismuth, lead, silver, tellurium, cadmium, and tin in the form of the metal and/or compounds thereof.

The platinum or palladium employed as catalyst can be used in any of the available forms, such as, for example, palladium black, platinum black, platinum oxide, palladium oxide, metallic platinum and metallic palladium, deposited on an inert support such as carbon black, charcoal, activated alumina, silica gel, asbestos, magnesium carbonate, calcium carbonate, and kieselguhr. Catalytic masses containing from 2% to 10% platinum or palladium on a support are particularly suitable.

The concentration of the methylol phenols in the aqueous solution should preferably be such that precipitation is avoided and a homogeneous solution is maintained throughout the reaction. A concentration of from 5% to 25% by weight is generally suitable.

The use of promoted catalyst systems of platinum-promoter or of palladium-promoter results in a significant improvement both in respect of the rate of reaction and in respect of the yields of aldehyde as compared to oxidation processes carried out in the presence of platinum or of palladium without the promoter. Thus, with platinum and bismuth a reduction is observed in the reaction time, which can become 20 times shorter, and an increase of 10 to 15% in the yields is observed. With palladium, the addition of the bismuth derivative promoter can make it possible to reduce the reaction time by a factor of about 8, with an increase of up to 10% in the yields. Furthermore, the use of the promoter makes it possible significantly to reduce the amount of Pt or Pd. For example, this quantity can be 5 to 10 times smaller, in the case of palladium, and even 25 times smaller, in the case of platinum.

The bismuth promoter generally employed is an inorganic or organic derivative of bismuth in which bismuth is at an oxidation level greater than zero, for example 2, 3, 4 or 5. The radical combined with the bismuth is not critical, provided it meets the above condition. The promoter can be soluble or insoluble in the reaction medium.

Illustrative bismuth promotors which can be used in the oxidation are bismuth oxides, bismuth hydroxides, salts of inorganic hydracids such as bismuth chloride, bromide, iodide, sulphide, selenide or telluride, salts of inorganic oxy-acids such as bismuth sulphite, sulphate, nitrite, nitrate, phosphite, phosphate, pyrophosphate, carbonate, perchlorate, antimonate, arsenate, selenite and selenate, salts of oxy-acids derived from transition metals such as bismuth vanadate, niobate, tantalate, chromate, molybdate, tungstate and permanganate.

Other suitable compounds are salts of aliphatic or aromatic organic acids such as bismuth acetate, propionate, benzoate, salicylate, oxalate, tartrate, lactate and citrate, and phenates such as bismuth gallate and bismuth pyrogallate. These salts and phenates can also be bismuthyl salts.

It is also possible to use binary combinations of bismuth with elements such as phosphorus and arsenic, and heteropolyacids containing bismuth, as well as their salts; aromatic and aliphatic bismuthines are also suitable.

Bismuth oxides include BiO; BiO$_3$; Bi$_2$O$_4$ and Bi$_2$O$_5$. Bismuth hydroxides include Bi(OH)$_3$.

Bismuth salts of inorganic halogen acids include bismuth chloride BiCl$_3$, bismuth bromide BiBr$_3$, bismuth iodide BiI$_3$, bismuth sulphide Bi$_2$S$_3$, bismuth selenide Bi$_2$Se$_3$, and bismuth telluride Bi$_2$Te$_3$.

Bismuth salts of inorganic oxy-acids include basic bismuth sulphite (Bi$_2$(SO$_3$)$_3$. Bi$_2$O$_3$5H$_2$O, neutral bismuth sulphate Bi$_2$(SO$_4$)$_3$, bismuthyl sulphate (BiO)HSO$_4$, bismuthyl nitrite (BiO)NO$_2$O5H$_2$O, neutral bismuth nitrate Bi(NO$_3$)$_3$5H$_2$O, the double nitrate of bismuth and magnesium 2 Bi(NO$_3$)$_3$3Mg(NO$_3$)$_2$24H$_2$O, bismuthyl nitrate (BiO)NO$_3$ bismuth phosphite Bi$_2$(PO$_3$H)$_3$3H$_2$O, neutral bismuth phosphate BiPO$_4$, bismuth pyrophosphate Bi$_4$(P$_2$O$_7$)$_3$, bismuthyl carbonate (BiO)$_2$CO$_3$5H$_2$O, neutral bismuth perchlorate Bi(ClO$_4$)$_3$5H$_2$O, bismuthyl perchlorate (BiO)ClO$_4$, bismuth antimonate BiSbO$_4$, neutral bismuth arsenate Bi(AsO$_4$)$_3$, bismuthyl arsenate (BiO) AsO$_4$5H$_2$O, and bismuth selenite Bi$_2$(SeO$_3$)$_3$.

Bismuth salts of oxy-acids derived from transition metals include bismuth vanadate BiVO$_4$, bismuth niobate BiNbO$_4$, bismuth tantalate BiTaO$_4$, neutral bismuth chromate Bi$_2$(CrO$_4$)$_3$3 H$_2$O, neutral bismuthyl chromate (BiO)$_2$CrO$_4$, bismuthyl dichromate (BiO)$_2$Cr$_2$O$_7$, bismuthyl hydrogen chromate H(BiO)CrO$_4$, bismuthyl potassium chromate (double salt) K (BiO)Cr$_3$O$_{10}$, bismuth molybdate (Bi$_2$(MoO$_4$)$_3$, bismuth tungstate Bi$_2$(WO$_4$)$_3$, bismuth sodium molybdate (double salt) NaBi(MoO$_4$)$_2$, and basic bismuth permanganate Bi$_2$O$_2$(OH)MnO$_4$.

Bismuth salts of aliphatic or aromatic organic acids include bismuth acetate Bi(C$_2$H$_3$O$_2$)$_3$, bismuthyl propionate (BiO)C$_3$H$_5$O$_2$, basic bismuth benzoate C$_6$H$_5$CO$_2$·Bi(OH)$_2$, bismuthyl salicylate C$_6$H$_4$CO$_2$(BiO) (OH), bismuth oxalate (C$_2$O$_4$)$_3$Bi$_2$, bismuth tartrate Bi$_2$(C$_4$H$_4$O$_6$)$_3$6H$_2$O, bismuth lactate (C$_6$H$_9$O$_5$)OBi7H$_2$O and bismuth citrate C$_6$H$_5$O$_7$Bi.

Bismuth phenates include basic bismuth gallate C$_7$H$_7$O$_7$Bi and basic bismuth pyrogallate C$_6$H$_3$(OH)$_2$(OBi) (OH).

Other inorganic or organic bismuth compounds which are also suitable are bismuth phosphide BiP, bismuth arsenide Bi$_3$As$_4$, sodium bismuthate NaBiO$_3$, the bismuththiocyanic acids H$_2$[Bi(CNS)$_5$] and H$_3$[Bi(CNS)$_6$], and their sodium and potassium salts, trimethylbismuthine Bi(CH$_3$)$_3$ and triphenylbismuthine Bi(C$_6$H$_5$)$_3$.

The bismuth derivatives used preferentially for carrying out the process according to the invention are the bismuth oxides, the bismuth hydroxides, the bismuth or bismuthyl salts of inorganic hydracids, the bismuth or bismuthyl salts of inorganic oxy-acids, the bismuth or bismuthyl salts of aliphatic or aromatic organic acids; and the bismuth or bismuthyl phenates.

A group of promoters which are particularly suitable for carrying out the invention consists of the bismuth oxides Bi$_2$O$_3$ and Bi$_2$O$_4$, bismuth hydroxide Bi(OH)$_3$, neutral bismuth sulphate Bi$_2$(SO$_4$)$_3$, bismuth chloride BiCl$_3$, bismuth bromide BiBr$_3$, bismuth iodide BiI$_3$, neutral bismuth nitrate Bi(NO$_3$)$_3$5H$_2$O, bismuthyl carbonate (BiO)$_2$CO$_3$O.5H$_2$O, bismuth acetate Bi(C$_2$H$_3$O$_2$)$_3$ and bismuthyl salicylate C$_6$H$_4$CO$_2$(BiO)(OH).

The lead promoter employed is an inorganic or organic derivative of lead in which the lead is at an oxidation level greater than 0, for example 2, 3, or 4. The radical combined with lead is not critical. The laed promoter can be soluble or insoluble in the reaction medium.

Illustrative lead promoters include lead acetate, basic lead acetate, lead formate, lead nitrate, lead oxalate, lead suboxide, lead monoxide, red lead oxide, lead sesquioxide, lead dioxide, lead sulfate, acid lead sulfate, and lead phenolate.

The silver promoter generally employed is an inorganic or organic derivative of silver, and again the radical combined with the silver is not critical. The silver promoter can be soluble or insoluble in the reaction medium.

Illustrative silver promoters include silver acetate, silver metaborate, silver oxide, silver nitrate, and silver sulfate.

The tellurium promoter is an inorganic or organic derivative of tellurium in which the tellurium is at an oxidation level greater than 0, for example 2 or 4. The radical combined with the tellurium is not critical, and the tellurium promoter can be soluble or insoluble in the reaction medium.

Illustrative tellurium compounds include tellurium hydroxide, tellurium oxide, tellurium dioxide, tellurium trioxide, tellurium oxysulfate, and tellurium basic nitrate.

The cadmium promoter is an inorganic or organic derivative of cadmium in which the cadmium is at an oxidation level greater than 0, for example 1 or 2. The radical combined with the cadmium is not critical, and the cadmium can be soluble or insoluble in the reaction medium.

Illustrative cadmium promoters include cadmium acetate, cadmium hydroxide, cadmium nitrate, cadmium lactate, cadmium oxalate, cadmium oxide, cadmium suboxide, cadmium sulfate, and cadmium telluride, CdTe.

The tin promoter is an inorganic or organic derivative of tin in which tin is at an oxidation level greater than 0, for example 2 or 4. The radical combined with the tin is not critical. The tin promoter can be soluble or insoluble in the reaction medium.

Illustrative tin promoters which can be used are stannous hydroxide, stannous oxalate, stannous oxide, stannous telluride SnTe, stannic oxide, and stannic sulfate.

The amount of promoter used, expressed as the amount of metal contained in the promoter, relative to the weight of the noble metal employed, can vary within wide limits, as low as 0.1% and as high as the weight of noble metal employed and even, without disadvantage, exceeding the latter.

More particularly, this amount is chosen so as to introduce into the oxidation medium from 10 to 900 ppm by weight of metallic promoter relative to the methylol phenol. In this connection, larger amounts of promoter, of the order of 900 to 1,500 ppm, can, of course, be used, but without major additional advantage.

The amount of catalyst employed, expressed in weight of metallic platinum or metallic palladium relative to that of the alcohol to be oxidized, can vary from about 0.01 to about 4% and preferably from 0.04 to 2%. The oxidation is carried out in an aqueous medium containing an alkaline reagent in solution. The alkali in the condensation reaction is of course used in the oxidation as well.

The reaction mixture is then brought to oxidation temperature within the range from about 0° to about 100° C., and preferably from about 30° to about 60° C., and oxygen or an oxygen-containing gas such as air is then admitted to the mixture. This can be done by bubbling or sparging the oxygen or oxygen-containing gas through the reaction mixture, or by stirring the mixture under an oxygen or oxygen-containing gas atmosphere.

Reaction is continued until the methylol groups are converted to aldehyde groups, which usually requires from about one-half hour to about ten hours, but the reaction can be continued as long as necessary to obtain the desired product.

The reaction will proceed at atmospheric pressure, but if desired superatmospheric pressures in a pressure vessel can be used.

The working-up of the reaction mixture to separate and recover the desired salicylaldehydes and p-hydroxybenzaldehyde or other aldehydes of the substituted phenol used as a starting material should be carefully controlled in order to avoid prejudicing the yield. The aldehydes are quite sensitive to polymerization, especially when heated.

First, the catalyst should be removed by centrifuging or filtration, and the pH of the reaction mixture then brought to within the range from about 7 to about 2, and preferably about 4, using an inorganic or organic acid, preferably sulfuric acid, to hydrolyze the phenolate and liberate the phenols, which accordingly separate out as a supernatant organic layer over an aqueous layer that contains inorganic salts and very little organic material. The organic layer contains the starting phenol, the mono and poly aldehydes, and most of the tars, and can be removed by decantation. The more volatile aldehydes can then be separated from the tars by flash distillation, preferably under reduced pressure, at a low enough temperature to be distilled out without appreciable decomposition. If fractional distillation is not feasible, because of heat sensitivity of the aldehyde compounds, or high temperature of the distillation, the aldehyde species can be separated by fractional crystallization from an appropriate solvent system.

Selective removal of unwanted CHO groups in the hydroxybenzene carboxaldehyde reaction products is accomplished by decarbonylation. In this way, the reaction products can be converted into more valuable materials. Thus, in preparing vanillin from guaiacol, a large amount of ortho-vanillin is also made; its conversion to guaiacol by decarbonylation is advantageous due to the limited market for ortho-vanillin. Another example is in the preparation of salicylaldehyde and p-hydroxybenzaldehyde. The 2,4- and 2,6- dialdehydes by decarbonylation yield a mixture of salicylaldehyde and phenol. The para-formyl species appears to decarbonylate faster than the ortho-formyl species.

It is known that aromatic aldehydes decarbonylate when heated over hydrogenation catalysts. Of the aromatic aldehydes containing a phenolic group, vanillin is reported to decarbonylate over nickel at 370°–390° C., giving guaiacol and catechol. It is reported (Synthesis, December, 1969, p. 164) that salicylaldehyde in refluxing toluene and in the presence of a stoichiometric amount of chloro-tris(triphenyl phosphine)-rhodium complex yields phenol in 70% yield.

The decarbonylation of some non-phenolic aromatic aldehydes in the presence of a palladium catalyst is described in *J. Am. Chem. Soc.* 90 94 (1968). As examples, PdO, PdCl$_2$ and palladium on carbon are given. An earlier publication, *J. Org. Chem.* 25 2215 (1960), reports a successful decarbonylation of o-methoxy-benzaldehyde over 1% Pd/C (5% Pd) at 243° C. to anisole, with a yield of 94%.

Decarbonylation of the hydroxybenzene carboxaldehydes, both mono- and poly-aldehyde species, obtained in the condensation of phenols and formaldehyde followed by oxidation departs from the normal course of decarbonylation in requiring a certain class of palladium catalyst at quite elevated temperature. For example, palladium oxide and palladium salts such as PdCl$_2$ or PdBr$_2$ are totally ineffective.

Metallic palladium is an effective catalyst, and so also is palladium hydroxide. The metallic palladium can take any form, such as palladium black and palladium metal. The metal can also be deposited on an inert support, such as carbon black, charcoal, activated alumina, silica gel, asbestos, magnesium carbonate, calcium carbonate, and kieselguhr.

The amount of catalyst is not critical. Small amounts are not always effective, and it appears that in most instances the amount should be at least about 0.5% by weight of the hydroxybenzene carboxaldehyde. The upper limit on the amount is set by the controllability of the reaction. The larger the amount of catalyst, the more rapid the reaction, which may be very difficult to control, if it is too rapid. Accordingly, an amount in excess of about 25% by weight of the carboxaldehyde would not normally be used. The preferred amount is within the range from about 0.5 to about 5% by weight of the hydroxybenzene carboxaldehyde.

The catalyst appears to suffer no appreciable loss in activity in the course of the process, and can be recycled indefinitely.

The decarbonylation proceeds at an elevated temperature. While decarbonylation takes place at temperatures below 25° C., the reaction is normally too slow to be practical. Thus, usually a temperature of above 75° C. would be used. As reaction temperature increases, so does the rate of reaction, and therefore the upper limit on the reaction temperature is set by the decomposition temperature of the reactants and/or the reaction products, and the temperature at which the reaction proceeds at so high a rate as to make control impossible. The preferred temperature is within the range from about 175° to about 225° C.

At these temperatures, the reaction system is liquid because the aldehyde is liquid. Consequently, the reaction is easily carried out by simply dispersing or distributing the catalyst within the liquid aldehyde, and continuing the reaction with stirring for as long as required, usually several hours, until the decarbonylation is complete.

The decarbonylation proceeds with liberation of carbon monoxide, and thus it is easy to follow the reaction by simply collecting the carbon monoxide. When the evolution of carbon monoxide ceases, i.e., the collected volume ceases to grow, or becomes constant, the reaction is as complete as it will be under those reaction conditions, and it will be necessary either to stop the reaction, or increase the reaction temperature, or increase the amount of catalyst, as required to effect the desired degree of decarbonylation. Thus, the reaction would normally be halted when the evolution of carbon monoxide gas ceases.

If the reaction is difficult to control, for any reason, the intensity of the reaction can be moderated by adding an inert solvent that is a liquid under reaction conditions, and does not poison the catalyst.

Exemplary solvents include the aliphatic, cycloaliphatic and aromatic hydrocarbons, aliphatic glycols and polyoxyalkylene glycols having a boiling point above the selected reaction temperature. If necessary, the reaction mixture can be kept under pressure, to maintain the solvent in the liquid phase.

In order to avoid subjecting the decarbonylation reaction product to high temperatures, after the phenol or phenol aldehyde is liberated at elevated temperature, the decarbonylation reaction product can be distilled out of the reaction mixture as it is formed in the course of the reaction. Addition of water to the reaction mixture will assist in such removal by steam-distilling the reaction product out of the mixture.

After the decarbonylation reaction has ceased, or is terminated, the catalyst can be separated by filtration, and the cake washed with solvent to remove reaction mixture. The filtrate and washings are then distilled, to recover the reaction product.

The following Examples in the opinion of the inventors represent preferred embodiments of the invention:

EXAMPLE 1

Preparation of Salicylaldehyde and para-Hydroxybenzaldehyde:

In this Example, the process was conducted batchwise in a pilot plant. The data given is for one pilot plant run.

Stage A. Condensation:

| Charges | Weight (g) | Moles |
|---|---|---|
| Phenol | 6770 | 72 |
| NaOH (49.8% aqueous solution) | 5785 | 72 |
| Water | 8615 | — |
| Formaldehyde (37.5% aqueous solution) | 2900 | 36 |

Procedure:

The phenol and aqueous sodium hydroxide were mixed and reacted to form sodium phenolate in aqueous solution, and the formaldehyde solution was then added slowly to the sodium phenolate solution at 50° C. At the end of 1 hour and 45 minutes, a sample of the reaction mixture was analyzed by liquid chromatography indicating the following composition:

| | % by Weight | g |
|---|---|---|
| Phenol | 16.6 | 4004 |
| o-Methylol phenol | 5.23 | 1259 |
| p-Methylol phenol | 5.93 | 1426 |

This corresponds to a direct yield of 30%, and a true yield of 74% of both o- and p-methylol phenols.

Stage B. Oxidation:

To this reaction mixture, without separation of any components, 59.5 g of 5% platinum on carbon and 1 g $Bi_2(SO_4)_3$ were added, and the system purged of air and fed with oxygen, keeping the temperature at 50° C., until absorption of oxygen stopped. The end of the oxidation is reached in 1 hour and 30 minutes, with a total of about 15 moles of oxygen absorbed, which represents about 84% of the theory based on the amount of methylol phenols as indicated by liquid chromatographic analysis (36 moles of methylol phenols requiring 18 moles of oxygen). The discrepancy could be due to inaccurate measure of the amount of oxygen. The reaction mixture, although not absorbing any more oxygen, was agitated and held at 50° C. for another 30 minutes, although this is not normally necessary. Filtration of the catalyst was accomplished in about 20 minutes through a sparkler filter, and the filtrate cooled to about 28° C. and acidified by addition of about 3750 g 93.2% aqueous sulfuric acid (35.7 moles), to bring the pH to about 4. The acidification took about 30 to 45 minutes, and the temperature was kept below 45° C. throughout. The organic layer was decanted.

Stage C. Recovery of the Phenol, Salicylaldehyde and para-Hydroxybenzaldehyde:

An aliquot of 500 g from this reaction mixture was placed in a 1 liter distilling flask equipped with a Claisen head, and distilled at 10 Torr in order to remove the phenol and the salicylaldehyde. Recovery of phenol and salicylaldehyde was in a 98% yield. The para-hydroxybenzaldehyde in the residue found after distillation represented 98% of the amount before distillation.

Following the above procedure, three pilot plant batches were prepared, each batch on a 72 mole scale, as indicated, to a total of 216 moles. The following analyses, material balance and yields were obtained:

(a) Prior to Oxidation

Direct yield 30% by liquid chromatographic analysis
True yield 73% by liquid chromatographic analysis (b) After Oxidation/Acidification

| | PHENOL | | | | ortho-Hydroxy-benzaldehyde | | | para-Hydroxy-benzaldehyde | | |
|---|---|---|---|---|---|---|---|---|---|---|
| | g | % | g | Moles | % | g | Moles | % | g | Moles |
| Organic (A) | 26600 | 44.71 | 11895 | 126.5 | 13.66 | 3633.5 | 29.8 | 14.71 | 3913 | 32 |

-continued

| | | |
|---|---|---|
| Aqueous a | 54995 | 333 |
| Aqueous b | 17800 | 28 |

Direct yield $\frac{62.64}{216} = 29\%$

Phenol "recovered": 126.5 + 3.8 = 130.3 mole
Phenol reacted: 216 − 130.3 = 85.7 mole True yield $\frac{62.64}{85.7} \times 100 = 73\%$ (c) After Flash Distillation of Phenol and zation from toluene or xylene, as exemplified for six runs in the following Table.

TABLE

| Run | Toluene | $g^5$ p-HB + Di | % p-HB | g p-HB | $g^4$ Crystals | % p-HB | Melting point °C. | g p-HB | % Recovered | g | Toluene Solubles % p-HB | g p-HB |
|---|---|---|---|---|---|---|---|---|---|---|---|---|
| 1 | 100 | 58.1 | 64.9 | 37.7 | 39.0 | 88.4 | 100–105° | 34.5 | 91.5 | 16.0 | 10.7 | 1.7 |
| 2[1] | 150 | 35.5 | 88.4 | 31.4 | 30.0 | 99.7 | 115–116° | 29.9 | 95.2 | 4.2 | 9.7 | 0.4 |
| 3 | 150 | 50.0 | 64.9 | 32.5 | 33.3 | 90.1[2] | 106–110° | 30.0 | 92.6 | 17.5 | 8.3 | 1.5 |
| 4 | 200 | 50.0 | 64.9 | 32.5 | 29.3 | 100.0 | 114–116° | 29.3 | 90.2 | 20.6 | 9.5 | 2.0 |
| 5 | 250 | 50.0 | 65.0 | 32.5 | 29.7 | 100.0 | 114–115.5° | 29.7 | 91.4 | 20.1 | 9.5 | 1.9 |
| 6[3] | 150 | 50.0 | 65.0 | 32.5 | 30.7 | 98.6 | 114–115.5° | 30.3 | 93.1 | | | | p-HB = para-hydroxybenzaldehyde
Di = Di-formyl phenols
[1]Recrystallization of product of Test 1
[2]Washed only once
[3]Repeat of Test 3 - two washes
[4]Saturated solutions cooled down to 25° C. before filtering
[5]Solubilization done at 85° C.

Salicylaldehyde:

The flash distillation was conducted with a 500 g charge, corresponding to 4.06 mol of phenol initially charged in the condensation step.

(d) After Distillation:
Gas Chromatographic Analysis

| | Weight g | Phenol % | Total | Salicyl- aldehyde % | Total | para- Hydroxy- benz- aldehyde % | Total | Other % | Total |
|---|---|---|---|---|---|---|---|---|---|
| Distillate | 366.4 | 59.42 | 217.7 | 18.26 | 66.9 | 0.586 | 2.15 | 1.02 | 3.75 |
| Pot Residue | 134.0 | 1.013 | 1.35 | 0.123 | 0.16 | 52.14 | 69.86 | 16.15 | 21.65 |
| Total | 500.4 | | 219.05 | | 67.06 | | 72.01 | | 25.4 |

| | Amount Expected | | Amount Obtained | |
|---|---|---|---|---|
| | g | Moles | g | Moles |
| Phenol | 223.6 | 2.38 | 219.05 | 2.33 |
| Salicylaldehyde | 68.3 | 0.56 | 67.06 | 0.549 |
| p-Hydroxybenz- aldehyde | 73.6 | 0.60 | 72.01 | 0.59 |

} 1.139

There was a 98% recovery of phenol, salicylaldehyde and para-hydroxybenzaldehyde.

Yield up to Stage (d):

$\frac{\text{Direct}}{\text{Yield}} = \frac{1.139}{4.06} \times 100 = 28\%$ $\frac{\text{True}}{\text{Yield}} = \frac{1.139}{3.97} \times 100 - 2.33 = \frac{1.139}{1.64} \times 100 = 69\%$ The separation of the para-hydroxybenzaldehyde from the 2,4 and 2,6- diformyl phenols and from the residues was accomplished by careful vacuum fractionation, in order to avoid decomposition, or by recrystallization from toluene or xylene, as exemplified for six runs in the following Table.

EXAMPLE 2

Preparation of Salicylaldehyde and para-Hydroxybenzaldehyde:

Stages A and B of Example 1 were repeated. Stage C was then modified as follows:

The crude reaction mixture obtained after acidification of pilot plant oxidation reaction mixture was fed continuously into a flash evaporator, separating three fractions:

(1) phenol and salicylaldehyde;
(2) residues; and
(3) fraction containing 60% para-hydroxybenzaldehyde, about 20% 2,4-diformyl phenol, 8% 2,6-diformyl phenol and 2% of 2,4,6-triformyl phenol.

Fraction 1 was separated into phenol and salicylaldehyde by fractional distillation or by steam distillation.

Fraction 2, the residues, was discarded.

Fraction 3, containing the desired hydroxybenzaldehyde reaction product, was mixed with five times its weight of toluene, and heated up to 80° to 90° C. Crystallization began upon cooling to about 75° to 80° C. and was completed at about 24° to 25° C. The crystals were filtered off and washed with toluene. Analysis of the crystals showed them 99% para-hydroxybenzaldehyde.

EXAMPLE 3

Preparation of Salicylaldehyde and para-Hydroxybenzaldehyde:

This process was conducted batchwise on a laboratory scale.

Stage A. Condensation:

| Reagents | Weight (g) | Moles |
|---|---|---|
| Phenol | 141.2 | 1.5 |
| Caustic Soda (49.6% aqueous solution) | 114.9 | 1.4 |
| Formaldehyde (36.6% aqueous solution) | 61.5 | 0.75 |

| Reagents | Weight (g) | Moles |
|---|---|---|
| Water | 203.1 | |

The phenol and 150 g H₂O were charged to a 1 liter Morton Flask fitted with a thermometer, stirrer, addition funnel and gas flow indicator. After purging with argon, the caustic was added slowly, under vigorous agitation. The remainder of the water was used to rinse the residual caustic into the reaction flask. The temperature was then raised to 50° C. and the formalin added dropwise over a 1 hour period. The mixture was maintained at 50° C. for an additional 45 minutes.

Stage B. Oxidation:

| Reagents | Weight (g) |
|---|---|
| Caustic Soda, 30% aqueous solution | 10.0 |
| 5% Platinum on carbon, dry | 0.83 |
| Bismuth sulfate | 0.0155 |
| $O_2$ - as needed | |

To the condensation reaction mixture, without separation of any components, an additional 10 g caustic soda was added, together with the catalyst. The oxidation was then started by introducing oxygen while agitating vigorously. The temperature was maintained at approximately 50° C. throughout the reaction, which was complete in two hours.

Stage C. Recovery of the Phenol, Salicylaldehyde and para-Hydroxybenzaldehyde:

After filtration of the catalyst, 520 cc of isopropyl ether was added and the pH of the solution brought to 6.8 by the addition of 78.9 g of 93% aqueous sulfuric acid. The insoluble material (2.32 g) was filtered off. Analysis showed the filtrate to be a mixture of 1.16 g 2,4,6-triformyl phenol, 0.50 g of 2,4 diformyl phenol and 0.50 g of para-hydroxybenzaldehyde. The aqueous layer after separation was further acidified to pH 4 which yielded 4.10 g of solids containing 3.2 g 2,4-diformyl phenol and 0.80 g 2,4,6-triformyl phenol.

The residue, after distillation of the phenol and the salicylaldehyde was subjected to recrystallization from toluene, thus affording one crop of 21 g pure p-hydroxybenzaldehyde and another one recovered from the mother liquor containing 2.5 g of p-hydroxybenzaldehyde, 5.0 g of 2,4-diformyl phenol and 2.5 g 2,6-diformyl phenol.

By analysis of all residual aqueous layers and products, the following materials were accounted for and yields calculated:

| | Phenol | p-Hydroxybenz-aldehyde | Salicyl-aldehyde | 2,4-Diformyl phenol | 2,6-Diformyl phenol | 2,4,6-Triformyl phenol |
|---|---|---|---|---|---|---|
| Yield g | 0.889 | 0.215 | 0.242 | 0.072 | 0.023 | 0.012 |
| Yield % | | 35.2 | 39.7 | 11.5 | 3.7 | 2.0 |

Total recovery of phenol and products amounted to 96.9% of theory. The recovery of the para-hydroxybenzaldehyde by this procedure amounted to 99% of theory.

The second crop of crystals contained 25% of p-hydroxybenzaldehyde with 50% 2,4-diformyl phenol and 25% of 2,6-diformyl phenol. These can be recrystallized to yield more pure parahydroxybenzaldehyde. The mixture of 2,4 and 2,6-diformyl phenol was subjected to decarbonylation.

Stage D. Decarbonylation:

A 2:1 mixture of 98% 2,4- and 2,6-diformyl phenol amounting to 12.32 g was placed with 0.4 g of palladium on carbon (10% Pd, 50% water) in a 250 ml flask, fitted with thermometer, addition funnel, water trap, and a direct vapor take-off for distilling. While heating the charge at 190° to 200° C., water was added to azeotrope the decarbonylated phenol. The distillate was extracted with ether. After evaporation of most of the solvent, 12.59 g of product was obtained. Analyses by gas chromatography and liquid chromatography indicated that the distillate contained 2.26 g phenol and 5.35 g salicylaldehyde, i.e., a yield of 84% of theory.

EXAMPLE 4

Preparation of Vanillin:

Stage A. Condensation:

Five moles of guaiacol (98% pure) 633.3 g were mixed with 2907 g of NaOH 7.02% aqueous solution (5.1 moles) and 165 g formaldehyde, 36.4% aqueous solution (2 moles). The reaction mixture was kept at 50° C. for five hours.

Stage B. Oxidation:

To this reaction mixture, without separation of any components, 6.67 g of 5% platinum on carbon mixed with 0.47 g of $Bi_2(SO_4)_3$ were added, together with 290 g of 7% aqueous NaOH solution. Oxygen was fed into the system under vigorous agitation, and the pot temperature maintained at 38°–40° C. In one hour and 10 minutes, 23.4 liters of oxygen was absorbed. After acidification to pH 2 with 47% aqueous sulfuric acid at 20° C., the two layers were separated, the aqueous layer extracted to recover organic material, and this combined with the organic layer. The organic material was recovered using the following procedure:

| | Weight (g) | Moles | Yield % |
|---|---|---|---|
| Guaiacol | 393.2 | 3.17 | — |
| Vanillin | 125.8 | .83 | 45.3 |
| o-Vanillin | 94.2 | .62 | 33.87 |
| Diformyl guaiacol | 43.3 | .24 | 13.11 |

After separation of the guaiacol and the vanillin by fractional distillation, the mixture of o-vanillin and diformyl guaiacol was decarbonylated.

Stage C. Decarbonylation of ortho-Vanillin and Diformyl-Guaiacol:

The mixture of 0.0619 mole of o-vanillin and 0.0214 mole of diformyl gauiacol (total 0.0838 mole) was decarbonylated in the presence of 2% platinum on carbon at 205° to 210° C. until 2030 cc of CO was collected. After filtration of the catalyst and distillation of the residual material, guaiacol 0.0501 mole, and 0.0206 mole of o-vanillin was found, corresponding to a yield of 80% in the decarbonylation reaction. The overall yield of vanillin after the decarbonylation of the o-vanillin and the diformyl guaiacol is therefore 73%. Without the decarbonylation, the yield is 45.3%.

EXAMPLE 5

Preparation of Ethyl Vanillin:

Stage A. Condensation:

A mixture of 704 g 2-ethoxyphenol (5.0 moles), 403 g NaOH 49.6% aqueous solution (5.0 moles), water 2570 g and 206 g formaldehyde 36.4% aqueous solution (2.5 moles) was mixed together over thirty minutes with stirring. The temperature stayed at 32° C. The mixture was left overnight under argon, and then analyzed. The following results were obtained:

Direct yield: 44%

True yield: nearly quantitative

Ratio of ethyl vanillyl alcohol, o-ethyl vanillyl alcohol and dimethylol ethoxy phenol 3.79: 3.94: 2.03.

Stage B. Oxidation:

After adding 6.67 g 5% platinum on carbon (50% water) and 0.47 g $Bi_2(SO_4)_3$, the condensation reaction mixture without separation of any components was oxidized at 47° to 50° C. in about three hours with the absorption of 33 liters of oxygen. Midway through the oxidation, 40 g of 49.6% aqueous NaOH was added.

Stage C. Recovery of Ethyl Vanillin:

After the oxidation was complete, the catalyst was filtered off. The reaction mixture was acidified at 10° C. to pH 4.8 with 420 g 50% aqueous sulfuric acid. The reaction mixture was then extracted at room temperature five times with 800 g of dichloroethane. Most of the solvent was removed, and 925 g of crude oil obtained.

The aqueous layer was further acidified to pH 1.9 with 58 g 50% aqueous sulfuric acid and then extracted four times with dichloroethane. A total of 35 g product was obtained.

The oil and extracts were combined, with a small amount of solvent to rinse the flask. Total weight of product was 1073.2 g.

An aliquot of 158.8 g was distilled, and yielded 110 g of distillate and 3 g of residue. Analysis of the distillate indicated the following results:

| Yield | Ethyl Vanillin | Ortho-Ethyl Vanillin | Diformyl 2-Ethoxy Phenol | Total |
|---|---|---|---|---|
| Direct | 14.8% | 16.8% | 7.2% | 38.8% |
| True | 37.3% | 42.6% | 18.1% | 98.0% |

EXAMPLES 6 to 23

The ratio of products obtained is determined by the conditions used in the condensation reaction, since the oxidation reaction merely converts methylol groups to aldehyde groups.

The following Examples illustrate the effects on the product ratio by varying the molar ratios of phenol and NaOH in the condensation reaction.

All reactions were run at 50° C. and 30% NaOH (20% NaOH if indicated*). The order of addition was phenol, caustic, formaldehyde (35 to 37% solution in water). The mixture was heated for one hour thirty minutes, then cooled, and analyzed by liquid chromatography.

| | | | | Relative Amount of Product | |
|---|---|---|---|---|---|
| | Moles | | | Dimethylol | o- + p- Monomethylol |
| Example | Phenol | NaOH | HCHO | Phenol | Phenol |
| 6 | 1.0 | 1.0 | 1.0 | 11.7 | 58 |
| 7 | 1.0 | 1.0[1] | 1.0 | 14.1 | 56.6 |
| 8 | 1.0 | 1.0* | 1.0 | 14.6 | 57.0 |
| 9 | 1.0 | 1.0 | 1.0 | 12.9 | 58.8 |
| 10 | 1.0 | 1.2 | 1.0 | 4.6 | 64.8 |
| 11 | 1.0 | 1.2 | 1.0 | 5.9 | 68.8 |
| 12 | 1.0 | 1.5 | 1.0 | 4.8 | 53.1 |
| 13 | 1.0 | 1.5 | 1.0 | 3.0 | 57 |
| 14 | 1.0 | 1.0 | 1.1 | 15.0 | 53.0 |
| 15 | 1.0 | 0.8 | 1.0 | 10.4 | 56.0 |
| 16 | 1.0 | 1.0* | 0.5 | 4.3 | 72.4 |
| 17 | 1.0 | 1.0 | 0.5 | 3.7 | 76.4 |
| 18 | 1.0 | 1.0 | 0.4 | 2.0 | 73.8 |

[1] KOH instead of NaOH.

When o- and p-monoformyl phenols are the desired products, the relative amount of formaldehyde should be kept at about 0.4 mole or below. Whenever diformyl phenols are desired, the amount of formaldehyde should be above 0.4, ranging up to 1.5 moles and more. There appears to be no advantage in using more or less than the stoichiometric amount of base in relation to the phenol; the stoichiometric amount seems to be satisfactory. In the oxidation, however, a 10 to 29% excess of NaOH is preferable.

The following Examples illustrate oxidations run at a molar ratio of phenol:NaOH:HCHO 1:1:0.5 at 50° C., varying the concentration of the NaOH. The product ratios refer to the oxidized mixtures. (Both Reaction A and B were carried out).

| | Solution of NaOH (%) | Oxidation Time (Hours) | Product Ratios | | |
|---|---|---|---|---|---|
| Example | | | Phenol | Salicyl-aldehyde | p-Hydroxy-benzaldehyde |
| 19 | 15 | 1.5 | 45.4 | 15.1 | 15.4 |
| 20 | 20 | 3.0 | 46.8 | 14.3 | 14.9 |
| 21 | 30 | 4.0 | 47.1 | 15.8 | 12.3 |
| 22 | 40 | 6.0[1] | 48.4 | 12.5 | 9.5 |
| 23 | 50 | 2 | | | |

[1] After three hours, the oxidation was only 50% complete. Water was added to speed up the oxidation.
[2] Oxidation very slow; reaction discontinued.

Examples 19 to 23 indicate the influence of the amount of water on the rate of reaction B.

EXAMPLES 24 to 54

These Examples illustrate condensations run with varying molar amounts of formaldehyde, while keeping the ratio of phenol:sodium hydroxide at 1:1. The condensations were carried out at reaction temperatures between 20° and 50° C., and samples were taken at various time periods. The Product Ratios are relative.

| | | | | Product Ratios | | |
|---|---|---|---|---|---|---|
| Example | Moles HCHO | Reaction Temperature (°C.) | Time (Min.) | para-Methylol Phenol | ortho-Methylol Phenol | 2,4 and 2,6-Dimethyl Phenols |
| 24 | 0.5 | 20 | 30 | 3.7 | 4.6 | 0.5 |
| 25 | 0.5 | 20 | 60 | 5.8 | 7.1 | 1.2 |
| 26 | 0.5 | 20 | 120 | 9.0 | 10.2 | 2.6 |
| 27 | 0.5 | 20 | 240 | 11.7 | 12.2 | 4.6 |
| 28 | 0.5 | 20 | 300 | 12.6 | 12.9 | 5.3 |
| 29 | 0.7 | 20 | 30 | 4.4 | 5.9 | 0.8 |
| 30 | 0.7 | 20 | 60 | 7.4 | 9.5 | 1.9 |

-continued

| Example | Moles HCHO | Reaction Temperature (°C.) | Time (Min.) | para-Methylol Phenol | ortho-Methylol Phenol | 2,4 and 2,6-Dimethyl Phenols |
|---|---|---|---|---|---|---|
| 31 | 0.7 | 20 | 120 | 10.9 | 12.5 | 4.5 |
| 32 | 0.7 | 20 | 240 | 14.2 | 14.6 | 8.4 |
| 33 | 0.7 | 20 | 300 | 15.1 | 14.8 | 9.9 |
| 34 | 1.0 | 20 | 30 | 5.4 | 7.8 | 1.2 |
| 35 | 1.0 | 20 | 60 | 8.9 | 11.8 | 3.3 |
| 36 | 1.0 | 20 | 120 | 12.7 | 15.1 | 7.4 |
| 37 | 1.0 | 20 | 240 | 17.2 | 16.5 | 13.3 |
| 38 | 1.0 | 20 | 300 | 12.2 | 16.8 | 15.5 |
| 39 | 1.0 | 30 | 15 | 6.9 | 9.5 | 1.9 |
| 40 | 1.0 | 30 | 30 | 10.3 | 13.7 | 4.2 |
| 41 | 1.0 | 30 | 60 | 14.0 | 16.4 | 8.2 |
| 42 | 1.0 | 30 | 120 | 17.0 | 16.4 | 16.2 |
| 43 | 1.0 | 50 | 15 | 15.1 | 19.3 | 15.5 |
| 44 | 1.0 | 50 | 30 | 16.7 | 19.3 | 20.9 |
| 45 | 1.0 | 50 | 60 | 17.5 | 18.7 | 25.3 |
| 46 | 1.0 | 50 | 120 | 17.7 | 18.4 | 25.9 |
| 47 | 0.7 | 50 | 15 | 13.2 | 16.0 | 7.8 |
| 48 | 0.7 | 50 | 30 | 15.7 | 17.2 | 13.0 |
| 49 | 0.7 | 50 | 60 | 16.3 | 17.3 | 14.6 |
| 50 | 0.7 | 50 | 120 | 16.5 | 17.3 | 15.2 |
| 51 | 0.5 | 50 | 15 | 11.2 | 14.1 | 5.3 |
| 52 | 0.5 | 50 | 30 | 12.9 | 15.3 | 7.3 |
| 53 | 0.5 | 50 | 60 | 13.6 | 15.7 | 8.0 |
| 54 | 0.5 | 50 | 120 | 13.6 | 15.7 | 8.3 |

EXAMPLES 56 to 61

The following data from a study of reaction kinetic of guaiacol-formaldehyde condensation are given for comparison. The sodium hydroxide was used as 20% solution, the formaldehyde as 35 to 70% solution.

| Example | 55 | 56 | 57 | 58 | 59 | 60 | 61 |
|---|---|---|---|---|---|---|---|
| Ratio Guaiacol: NaOH:HCHO | 1:1:0.5 | | | 1:1:1 | 1:1:1.5 | 1:1:2 | 1:1:3 |
| Time (hours) | 4½ | | | 5 | 4½ | 4½ | 4½ |
| Temperature (°C.) | 20 | 30 | 50 | 30 | 20 | 20 | 20 |
| PRODUCT RATIOS | | | | | | | |
| Dimethylol guaiacol | 1.57 | 2.87 | 2.72 | 7.67 | 6.35 | 11.97 | 11.19 |
| Vanillyl alcohol | 3.91 | 4.73 | 4.39 | 6.03 | 4.52 | 3.64 | 3.19 |
| o-Vanillyl alcohol | 3.79 | 4.99 | 4.86 | 6.99 | 5.41 | 4.58 | 4.22 |
| Guaiacol | 12.66 | 13.41 | 11.32 | 5.97 | 5.11 | 2.18 | 1.52 |

A higher ratio of formaldehyde in the reaction mixture increases the di-substitution. It appears that the ratio of ortho to para-monomethylol derivatives is not changed greatly by varying the amount of formaldehyde. Increasing the reaction temperature from 30° to 50° C. affected the composition less than increasing from 20° to 30° C.

EXAMPLES 62 to 67

A number of phenols were reacted with formaldehyde in a mole ratio of 1.0:0.5. One mole of sodium hydroxide was used in each case. All reactions were run on 0.5 mole scale. After oxidation in the presence of Pt/C+Bi$_2$(SO$_4$)$_3$ catalyst, filtration and acidification, the products were extracted and flash-distilled.

| Example No. | Phenolic Compound | Products |
|---|---|---|
| 62 | catechol | Mostly monoformyl derivatives, predominantly ortho. Some diformyl derivatives also formed. |
| 63 | p-cresol | High yield of 4-hydroxy-5-formyl-toluene and some 3,5-diformyl-4-hydroxy toluene. |
| 64 | p-methoxy phenol | Predominantly 2-hydroxy-5-methoxy benzaldehyde and some 2,6-diformyl-4-methoxy-phenol. |
| 65 | 2,6-dimethyl-phenol | High yield of 3,5-dimethyl-4-hydroxy benzaldehyde. |
| 66 | o-cresol | Both o- and p-formyl derivatives, and substantial amount of the 4,6-diformyl derivative. |
| 67 | p-chlorophenol | Both mono and diformyl derivatives produced. |

EXAMPLES 68 to 72

Phenol, 984.8 g (10.46 moles) was condensed with 422.8 g 37.0% (4.1 mol) aqueous formaldehyde solution under an argon atmosphere in the presence of 891.2 g 49.5% (11.02 mol) aqueous NaOH solution and 1003.4 g H$_2$O. The mixture was stirred for 1.5 hours at a pot temperature range of 65° to 55° C. and held for an additional 1.5 hours at 55° C.

Analysis revealed that 641.8 g of phenol remained unchanged, and 170.4 g saligenol and 152 g p-hydroxybenzylalcohol were formed.

Aliquots of this reaction mixture were used in the oxidation reactions below. The data indicate the influence of the composition of the catalyst on the reaction rate.

| Example No. | Aliquot (g) | Catalyst | Volume O$_2$ consumed (liters) | Time | Temp. (°C.) |
|---|---|---|---|---|---|
| 68 | 331.6 | 0.84 g 5% Pt/C 0.024 g Bi$_2$(SO$_4$)$_3$ 4.15 g aq. 49.4% NaOH | 5.0 | 3 hours 10 minutes | 55 |
| 69 | 330.9 | 0.84 g 5% Pt/C 0.13 g Pb(OAC)$_2$ . 3H$_2$O 20 ml 1 N. NaOH | 4.7 | 3 hours 25 minutes | 55 |
| 70 | 334.5 | 1.67 g 5% Pd/C.50% H$_2$O 0.13 g Pb(OAC)$_2$. 3H$_2$O 20.0 ml 1 N. naOH | 4.2 | 4 hours 0 minutes | 55 |
| 71 | 279.4 | 1.68 g 5% Pd/C . 50% H$_2$O 8.91 g 49.4% aq NaOH | 4.8 | 7½ hours* | 56 |
| 72 | 277.4 | 1.68 g 5% Pd/C . 50% H$_2$O 8.32 g 49.4% aq. NaOH 0.02325 g Bi$_2$(SO$_4$)$_3$ | 5.0 | 4.5 hours | 56 |

*Longer run time probably due to less efficient stirring.

Having regard to the foregoing disclosure, the following is claimed as inventive and patentable embodiments thereof:

1. A process for the preparation of hydroxy benzene carboxaldehydes having the formula:

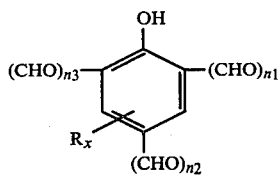

wherein:
R is selected from the group consisting of alkyl, alkoxy, cycloalkyl, aryl, alkoxyalkyl, fluoroalkyl, and hydroxyalkyl oxyalkylene having from one to about twenty carbon atoms; hydroxyalkyl having at least two to about twenty carbon atoms; hydroxy; aldehyde CHO; and halogen;

$n_1$, $n_2$ and $n_3$ are zero or 1; and at least one of $n_1$, $n_2$ and $n_3$ is 1; and x is zero, 1, 2, 3, or 4, which comprises:

(1) condensing with a formaldehyde compound a phenol having the formula:

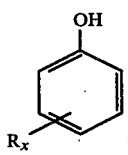

wherein
R is selected from the group consisting of alkyl, alkoxy, hydroxyalkyl, cycloalkyl, aryl, alkoxyalkyl, fluoroalkyl, and hydroxyalkyl oxyalkylene having from one to about twenty carbon atoms; hydroxy; and halogen; and x is zero, 1, 2, 3 or 4, and unsubstituted in at least one ortho or para position in an aqueous reaction medium comprising phenol:HCHO in a molar ratio within the range from about 1:0.1 to about 1:3 and alkali in a molar ratio alkali:phenol within the range from about 1:0.1 to about 1:2 and an alkali concentration not exceeding 30% by weight at a temperature within the range from about 0° to about 120° C. and obtaining a reaction mixture comprising a mixture of monomethylol and polymethylol phenols having the formula:

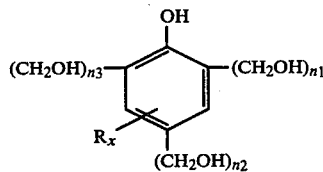

wherein
R is selected from the group consisting of alkyl, alkoxy, hydroxyalkyl, cycloalkyl, aryl, alkoxyalkyl, fluoroalkyl, and hydroxyalkyl oxyalkylene having from one to about twenty carbon atoms; hydroxy; and halogen;

$n_1$, $n_2$ and $n_3$ are zero or 1; and at least one of $n_1$, $n_2$ and $n_3$ is 1; and x is zero, 1, 2, 3 or 4;

(2) subjecting the reaction mixture without separation of the monomethylol species from polymethylol species to oxidation under conditions favoring oxidation of methylol species to the corresponding aldehyde species in the presence of oxygen and an amount of alkali that is at least stoichiometrically equal to the amount of phenol and a platinum or palladium oxidation catalyst, at a temperature within the range from about 0° to about 100° C. and a pH within the range from about 11 to about 13.5;

(3) separating and recovering the desired aldehyde in the reaction mixture;

(4) selectively decarbonylating to a corresponding phenol undesired aldehyde species to remove all or selected aldehyde groups in selected ring positions by heating the aldehyde species at a temperature within the range from about 75° to about 275° C. in the presence of a palladium catalyst selected from the group consisting of metallic palladium and palladium hydroxide; and then (5) recycling the phenol as starting phenol to step (1).

2. A process according to claim 1 in which the formaldehyde compound is an aqueous solution of formaldehyde in a formaldehyde concentration within the range from about 20 to about 37%.

3. A process according to claim 1 in which the formaldehyde compound is paraformaldehyde.

4. A process according to claim 1 in which the molar ratio phenol to formaldehyde is within the range from about 1:0.2 to about 1:3.

5. A process according to claim 1 in which the molar ratio of phenol:alkali is within the range from about 1:0.8 to about 1:1.2.

6. A process according to claim 1 in which the alkali is sodium hydroxide.

7. A process according to claim 1 in which the alkali is potassium hydroxide.

8. A process according to claim 1 in which the aqueous alkali solution is added to the phenol, and then the formaldehyde compound is added, and heat is then applied and reaction continued until the methylol phenol derivatives are formed.

9. A process according to claim 1 in which the condensation reaction is carried out at a temperature within the range from about 50° to about 75° C. for a reaction time within the range from about one-half hour to about fifteen hours.

10. A process according to claim 1 in which in the oxidation of the methylol phenols to the corresponding phenolic aldehydes, the amount of alkali is adjusted to an at least 10% excess of a 1:1 phenol:alkali molar ratio.

11. A process according to claim 10 in which the phenol:alkali ratio is within the range from about 1:1.1 to about 1:2.

12. A process according to claims 10 or 11 in which alkali in excess of the stoichiometric amount is added during the course of the oxidation reaction.

13. A process according to claim 1 in which during the oxidation the amount of water is within the range from about 3 to about 30 moles per mole of phenate.

14. A process according to claim 1 in which during the oxidation the amount of water is within the range from about 6 to about 10 moles per mole of phenate.

15. A process according to claim 1 in which the oxidation catalyst comprises a promoter.

16. A process according to claim 15 in which the catalyst is supported on an inert carrier and the promoter is selected from the group consisting of bismuth, lead, silver, tellurium, cadmium, and tin in the form of the metal and/or compounds thereof.

17. A process according to claim 15 in which the catalyst is supported on an inert carrier and the promoter is bismuth or a bismuth compound.

18. A process according to claim 1 in which the platinum or palladium catalyst is selected from the group consisting of palladium black, platinum black, platinum oxide, palladium oxide, metallic platinum and metallic palladium, on an inert support selected from the group consisting of carbon black, charcoal, activated alumina, silica gel, asbestos, magnesium carbonate, calcium carbonate, and kieselguhr in an amount within the range from about 5% to about 10% platinum or palladium based on the support.

19. A process according to claim 1 in which during the oxidation the concentration of the methylol phenol in the aqueous solution is within the range from about 10% to about 25% by weight, so that precipitation is avoided and a homogeneous solution is maintained throughout the reaction.

20. A process according to claim 1 in which the catalyst is a promoted catalyst system of platinum-promoter or of palladium-promoter in which the promoter is selected from the group consisting of bismuth, lead, silver, tellurium, cadmium, and tin in the form of the metal and/or compounds thereof.

21. A process according to claim 20 in which the promoter is in substantially equimolecular quantities in relation to the methylol phenol.

22. A process according to claim 20 in which the catalyst is a promoted catalyst system of platinum/bismuth or of palladium/bismuth.

23. A process according to claim 22 in which the bismuth promoter is an inorganic or organic derivative of bismuth in which bismuth is at an oxidation level within the range from 2 to 5.

24. A process according to claim 1 in which the reaction mixture is brought to oxidation temperature within the range from about 30° C. to about 60° C., oxygen or an oxygen-containing gas is admitted to the mixture, and reaction is continued until methylol groups are converted to aldehyde groups, for a time within the range from about one-half hour to about ten hours.

25. A process according to claim 1 in which the oxidation reaction is carried out at atmospheric pressure.

26. A process according to claim 1 in which the oxidation reaction is carried out at superatmospheric pressures in a pressure vessel.

27. A process according to claim 1 in which the working-up of the reaction mixture to separate and recover the mono and polycarboxy benzaldehydes of the starting phenol includes the steps of:
 (a) removing the catalyst;
 (b) bringing the pH of the reaction mixture to within the range from about 7 to about 2 by addition of an inorganic or organic acid, in an amount to hydrolyze the phenolate and liberate the phenols;
 (c) separating the reaction mixture into an organic layer comprising mono and polycarboxy benzaldehydes and tars, and an aqueous layer that contains inorganic salts and some organic material;
 (d) separating the two layers; and
 (e) flash distilling the aldehydes from the tars at a low temperature to minimize decomposition.

28. A process according to claim 1 in which the working-up of the reaction mixture to separate and recover the hydroxy benzaldehydes of the starting phenol includes the steps of:
 (a) removing the catalyst;
 (b) bringing the pH of the reaction mixture to within the range from about 7 to about 2 by addition of an inorganic or organic acid, in an amount to hydrolyze the phenolate and liberate the phenols;
 (c) separating the reaction mixture into an organic layer comprising hydroxy benzaldehydes and tars, and an aqueous layer that contains inorganic salts and some organic material;
 (d) separating the two layers; and
 (e) separating the aldehyde species by fractional crystallization from an aldehyde solvent system.

* * * * *